United States Patent
Wang et al.

(10) Patent No.: US 8,394,847 B2
(45) Date of Patent: *Mar. 12, 2013

(54) METHODS OF TREATING AN INFLAMMATORY-RELATED DISEASE

(75) Inventors: Longgui Wang, Flushing, NY (US); Xiao Mei Liu, Flushing, NY (US); Lian Mo, Palo Alto, CA (US); Simon K. Mencher, New York, NY (US); James P. McCarron, Jr., New York, NY (US)

(73) Assignee: Natrogen Therapeutics International, Inc., New York, NY (US)

( * ) Notice: Subject to any disclaimer, the term of this patent is extended or adjusted under 35 U.S.C. 154(b) by 402 days.

This patent is subject to a terminal disclaimer.

(21) Appl. No.: 12/548,083

(22) Filed: Aug. 26, 2009

(65) Prior Publication Data

US 2009/0325895 A1    Dec. 31, 2009

Related U.S. Application Data

(63) Continuation of application No. 11/104,422, filed on Apr. 13, 2005, now Pat. No. 7,582,670, which is a continuation-in-part of application No. 10/754,547, filed on Jan. 12, 2004, now abandoned, and a continuation-in-part of application No. 10/864,458, filed on Jun. 10, 2004, now Pat. No. 6,933,315, which is a continuation of application No. PCT/US02/39866, filed on Dec. 13, 2002, which is a continuation-in-part of application No. 10/021,589, filed on Dec. 13, 2001, now Pat. No. 6,566,341.

(60) Provisional application No. 60/407,267, filed on Sep. 3, 2002.

(51) Int. Cl.
*A01N 43/38* (2006.01)
*A01N 43/12* (2006.01)
*A01N 43/06* (2006.01)
*A61K 31/40* (2006.01)
*A61K 31/38* (2006.01)
*A61K 31/105* (2006.01)

(52) U.S. Cl. ........ 514/414; 514/415; 514/412; 514/443; 514/448; 514/421

(58) Field of Classification Search ....................... None
See application file for complete search history.

(56) References Cited

PUBLICATIONS

Tu Caixia et al. "A Study on the Pharmacological Activities of 4 Kinds of Di-Indole Compounds and Exploration of Its Clinical Significance", Chinese J. Derm., 1991, vol. 24, issue 4, pp. 245-247.*
Najarian et al. ("Connections between psoriasis and Crohn's disease", J.Am.Acad.Dermatol., 2003, vol. 48, pp. 805-821.*
Silverman, The Organic Chemistry of Drug Design and Drug Action, 2nd ed., 2004, pp. 25-34.*
Patani et al. "Bioisosterism: A Rational Approach in Drug Design", Chem.Rev., 1996, vol. 96, pp. 3147-3176.*
Kawai et al. "Structure-activity relationship study of novel NR2B-selective antagonists with arylamides to avoid reactive metabolites formation", Bioorg.Med.Chem.Lett., 2007, vol. 17, pp. 5537-5542.*

* cited by examiner

*Primary Examiner* — James D Anderson
*Assistant Examiner* — Stephanie Springer
(74) *Attorney, Agent, or Firm* — Rodney J. Fuller; Booth Udall Fuller, PLC

(57) ABSTRACT

The invention relates to pharmaceutical compositions and methods of treating inflammatory-related diseases associated with pro-inflammatory cytokine expression and/or reduced expression of anti-inflammatory cytokines. The method typically comprises administration of one or more compounds selected from isoindigo, indigo, indirubin, or derivatives thereof, such as, Meisoindigo and NATURA. Preferably the pharmaceutical composition comprises one or more compounds selected from isoindigo, indigo, indirubin, or derivatives thereof, an anti-inflammatory agent, and a pharmaceutically acceptable carrier.

14 Claims, 8 Drawing Sheets

METHODS OF TREATING AN INFLAMMATORY-RELATED DISEASE

CROSS-REFERENCE TO RELATED APPLICATIONS

This application is a continuation of U.S. patent application Ser. No. 11/104,422, filed Apr. 13, 2005, which is a continuation-in-part of U.S. patent application Ser. No. 10/754,547, filed Jan. 12, 2004 and U.S. patent application Ser. No. 10/864,458, filed Jun. 10, 2004, now U.S. Pat. No. 6,933,315, which is a continuation of International Application PCT/US02/39866 filed Dec. 13, 2002, which claims the benefit of U.S. Provisional Application No. 60/407,267 filed Sep. 3, 2002 and is a continuation-in-part of U.S. patent application Ser. No. 10/021,589, filed Dec. 13, 2001, now U.S. Pat. No. 6,566,341, the content of each of which is expressly incorporated herein by reference thereto.

TECHNICAL FIELD

The invention relates to pharmaceutical compositions and methods of treating inflammatory-related diseases associated with pro-inflammatory cytokine expression and/or reduced expression of anti-inflammatory cytokines. The method typically comprises administration to a subject in need thereof one or more compounds selected from isoindigo, indigo, indirubin, or derivatives thereof, such as, Meisoindigo and NATURA.

BACKGROUND OF THE INVENTION

Irregular and/or abnormal inflammation is a major component of a wide range of human diseases. People suffering from multiple degenerative disorders often exhibit excess levels of pro-inflammatory markers in their blood. One type of such pro-inflammatory markers are pro-inflammatory mark cytokines including IL-1$\alpha$, $\beta$, IL-2, IL-3, IL-6, IL-7, IL-9, IL-12, IL-17, IL-18, TNF-$\alpha$, LT, LIF, Oncostatin, and IFNc1$\alpha$, $\beta$, $\gamma$.

A non-limiting list of common medical problems that are directly caused by inflammatory cytokines include: arthritis where inflammatory cytokines destroy lead to lesion in the synovial membrane and destruction of joint cartilage and bone; kidney failure where inflammatory cytokines restrict circulation and damage nephrons; lupus wherein inflammatory cytokines induce an autoimmune attack; asthma where inflammatory cytokines close the airway; psoriasis where inflammatory cytokines induce dermatitis; pancreatitis where inflammatory cytokines induce pancreatic cell injury; allergy where inflammatory cytokines induce autoimmune reactions; fibrosis where inflammatory cytokines attack traumatized tissue; surgical complications where inflammatory cytokines prevent healing; anemia where inflammatory cytokines attack erythropoietin production; and fibromyalgia where inflammatory cytokines are elevated in fibromyalgia patients. Other diseases associated with chronic inflammation include cancer, which is caused by chronic inflammation; heart attack where chronic inflammation contributes to coronary atherosclerosis; Alzheimer's disease where chronic inflammation destroys brain cells; congestive heart failure where chronic inflammation causes heart muscle wasting; stroke where chronic inflammation promotes thrombo-embolic events; and aortic valve stenosis where chronic inflammation damages heart valves. Arteriosclerosis, osteoporosis, Parkinson's disease, infection, inflammatory bowel disease including Crohn's disease and ulcerative colitis as well as multiple sclerosis (a typical autoimmune inflammatory-related disease) are also related to inflammation (1-18). Some diseases in advanced stages can be life threatening. Several methodologies are available for the treatment of such inflammatory diseases; the results, however, are generally unsatisfactory as evidenced by a lack of efficacy and drug related side effects associated therewith.

Inflammatory Bowel Disease

Inflammatory bowel disease (IBD) comprises Crohn's disease (CD) and ulcerative colitis (UC), both of which are idiopathic chronic diseases occurring with an increasing frequency in many parts of the world. In the United States, more than 600,000 are affected every year. IBD can involve either or both small and large bowel. CD can involve any part of the gastrointestinal tract, but most frequently involves the distal small bowel and colon. It either spares the rectum, or causes inflammation or infection with drainage around the rectum. UC usually causes ulcers in the lower part of the large intestine, often starting at the rectum. Symptoms vary but may include diarrhea, fever, and pain. Patients with prolonged UC are at an increased risk of developing colon cancer.

There is currently no satisfactory treatment, as the cause for IBD remains unclear although infectious and immunologic mechanisms have been proposed. IBD treatments aim at controlling inflammatory symptoms, conventionally using corticosteroids, aminosalicylates and standard immunosuppressive agents such as azathioprine (6-mer-captopurine), methotrexate and ciclosporine. Of these, the only disease-modifying therapies are the immunosuppressive agents azathioprine and methotrexate, both of which have a slow onset of action and only a moderate efficacy. Long-term therapy may cause liver damage (fibrosis or cirrhosis) and bone marrow suppression. Also patients often become refractory to such treatment. Other therapeutic regimes merely address symptoms (19, 20).

Psoriasis

Psoriasis is one of the most common immune-mediated chronic skin diseases that come in different forms and varied levels of severity, affecting approximately 2% or more than 4.5 million people in the United States of which 1.5 million are considered to have a moderate to severe form of the disease. Ten to thirty percent of patients with psoriasis also develop a form of arthritis—Psoriatic arthritis, which damages the bone and connective tissue around the joints. Psoriasis appears as patches of raised red skin covered by a flaky white buildup. It may also have a pimple-ish (pustular psoriasis) or burned (erythrodermic) appearance. Psoriasis may also cause intense itching and burning. Patients suffer psychologically as well as physically. Several modalities are currently available for treatment of psoriasis, including topical treatment, phototherapy, and systemic applications. However, they are generally considered to be only disease suppressive and disease modifying. And none of them are curative. Moreover, many treatments are either cosmetically undesirable, inconvenient for long-term use, or associated with significant toxicity.

With increased understanding of the biological properties of psoriasis over the past 2 decades, biologic therapies targeting the activity of T lymphocytes and cytokines responsible for the inflammatory nature of this disease have become available. Currently, drugs prescribed for psoriasis include those TNF-$\alpha$ inhibitors initially used for rheumatoid arthritis (RA) treatment, ENBREL® (etanercept), REMICADE® (infliximab) and HUMIRA® (adalimumab), and T-cell inhibitor AMEVIVE® (alefacept) from Biogen approved in 2002 and RAPTIVA® from (Efalizumab) from Genentech/Xoma approved in 2003 (21). AMEVIVE ALEFACEPT® is an immunoglobulin fusion protein composed of the first extracellular domain of human LFA-3 fused to the hinge, C(H)2 and C(H)3 domains of human IgG(1). It inhibits T cell proliferation through NK cells (22). RAPTIVA® is also known as anti-CD11a, a humanized monoclonal antibody which targets the T cell adhesion molecule, leukocyte function-associated antigen-1 (LFA-1). Prevention of LFA-1 binding to its ligand (ICAM-1, intercellular adhesion molecule-1) inhibits lymphocyte activation and migration, resulting in a decreased lymphocyte infiltration, thereby limiting the cascade of events eventually leading to the signs and symptoms of psoriasis (23). Potential side effects for TNF-α inhibitor, however, are severe, including development of lymphoma (24), worsening congestive heart failure, resulting in a serious infection and sepsis, and exacerbations of multiple sclerosis and central nervous system problems (25, 26). While side effects of the T-cell inhibitor of AMEVIVE®/RAPTIVA® may be more tolerable in psoriasis treatment, RAPTIVA® is an immunosuppressive agent. Immunosuppressive agents have the potential to increase the risk of infection, reactivate latent, chronic infections or increase the risk of cancer development.

Although many advances have been made in the understanding of the biological properties of psoriasis over the past 2 decades and an unconventional treatment for psoriasis has become available as described above, much of the suffering it produces is still not adequately addressed. A survey of over 40,000 American patients with psoriasis performed by the National Psoriasis Foundation in 1998 showed 79% of the younger patients felt frustrated by the ineffectiveness of their treatment. Of those with severe disease, 32% felt their treatment was not aggressive enough (27, 28).

Rheumatoid Arthritis

Rheumatoid arthritis (RA) represents another example of troublesome inflammatory disorders. It is a common chronic inflammatory-related disease characterized by chronic inflammation in the membrane lining (the synovium) of the joints and/or other internal organs. The inflammatory cells can also invade and damage bone and cartilage. The joint involved can lose its shape and alignment, resulting in loss of movement. Patients with RA have pain, stiffness, warmth, redness and swelling in the joint, and other systemic symptoms like fever, fatigue, and anemia. Approximately 1% of the population or 2.1 million in the U.S. are currently affected, of which more are women (1.5 million) than men (0.6 million). The pathology of RA is not fully understood although the cascade of improper immunological reactions has been postulated as a mechanism. Conventional treatment is unfortunately inefficient in RA (29). The disease does not respond completely to symptomatic medications including corticosteroids and non-steroidal anti-inflammatory drugs (NSAIDs) used since the 1950s. Also, these medications carry a risk of serious adverse effects. The therapeutic effects of the disease-modifying antirheumatic drugs (DMARDs) such as Methotrexate (MTX) are often inconsistent and short-lived.

A new class of biologic DMARDs (disease-modifying antirheumatic drugs) for the treatment of RA has recently been developed based on understanding of the role of cytokines, TNF-α and IL-1, in the inflammatory process. The FDA has approved several such DMARDs including ENBREL® (etanercept) from Immunex/Amgen Inc. in 1998, REMICADE® (infliximab) from Centocor/Johnson & Johnson, HUMIRA® (adalimumab) from Abbott Laboratories Inc. in 2002, and KINERET® (anakinra) from Amgen in 2001. ENBREL® is a soluble TNF receptor (TNFR) recombinant protein. REMICADE® is a humanized mouse (chimeric) anti-TNF-α monoclonal antibody. HUMIRA® is a fully human anti-TNF monoclonal antibody created using phage display technology resulting in an antibody with human-derived heavy and light chain variable regions and human IgG1:k constant regions. All these 3 protein-based drugs target and bind to TNF-α to block the effects of TNF-α. KINERET® is a recombinant IL-1 receptor antagonist, which is similar to native human IL-1Ra, except for the addition of a single methionine residue at its amino terminus. KINERET® blocks the biologic activity of IL-1 by competitively inhibiting IL-1 binding to the IL-1 type I receptor (IL-1RI) and consequently reducing the pro-inflammatory effects of IL-1.

The treatment with these biologic DMARDs relieves symptoms, inhibits the progression of structural damage, and improves physical function in patients with moderate to severe active RA. The 3 marketed TNF-α blocking agents have similar efficacy when combined with MTX, a widely used DMARD, in the treatment of patients with RA (30). While providing significant efficacy and a good overall safety profile in the short and medium term in many patients with RA, these biologic treatments may create serious problems and long-term side effects, such as on the liver, and still need to be evaluated. There has been a disturbing association between the use of both of ENBREL® or REMICADE® and the development of lymphoma (24). As described above, several reports have shown that patients treated with ENBREL® or REMICADE® worsen their congestive heart failure and develop serious infection and sepsis, and increase exacerbations of multiple sclerosis and other central nervous system problems (26, 27).

Multiple Sclerosis

Multiple Sclerosis (MS) is an autoimmune disease diagnosed in 350,000 to 500,000 people in the United States. Multiple areas of inflammation and scarring of the myelin in the brain and spinal cord signify the disease. Patients with MS exhibit varied degrees of neurological impairment depending on the location and extent of the scarring of the myelin. Common symptoms of MS include fatigue, weakness, spasticity, balance problems, bladder and bowel problems, numbness, vision loss, tremors and depression. Current treatment of MS only alleviates symptoms or delays the progression of disability, and several new treatments for MS including stem cell transplantation and gene therapy are conservatory (31, 32). While anti-TNF antibodies have shown protective effects in experimental autoimmune encephalomyelitis (EAE), they aggravate the disease in MS patients, suggesting that inhibition of TNF-α alone is not sufficient (33).

Neurodegenerative Disorders

Alzheimer's disease (AD) and Parkinson's disease (PK) are the 2 most common neurodegenerative disorders. AD is a brain disorder. It seriously affects a person's ability to carry out daily activities. It involves the parts of the brain that control thought, memory, and language. About 4 million Americans, usually after age 60, are estimated to suffer from AD.

PK is a progressive disorder of the central nervous system affecting over 1.5 million people in the United States. Clinically, the disease is characterized by a decrease in spontaneous movements, gait difficulty, postural instability, rigidity and tremor. PK is caused by the degeneration of the pigmented neurons in the substantia nigra of the brain, resulting in decreased dopamine availability. The causes of these neurodegenerative disorders are unknown and there is currently no cure for the disease.

Thus, novel approaches for the treatment of the above and other inflammatory-related diseases are needed. Although the mechanisms by which inflammatory-related diseases are caused remain unclear, and often vary from each other, dysfunction of the immune system caused by deregulation of cytokines has been demonstrated to play an important role in the initiation and progression of inflammation (Table 1) (27, 34, 35).

Cytokines can be generally classified into 3 types: pro-inflammatory (IL-1α, β, IL-2, IL-3, IL-6, IL-7, IL-9, IL-12, IL-17, IL-18, TNF-α, LT, LIF, Oncostatin, and IFNc1α, β, γ,); anti-inflammatory (IL-4, IL-10, IL-11, W-13 and TGFβ); and chemokines (IL-8, Grooc, MIP-1, MCP-1, ENA-78, and RANTES).

In many inflammatory conditions, pro-inflammatory cytokines, especially TNF-α, IL-1β, and IL-6, as well as anti-inflammatory cytokine IL-10 appear to play an important role in the pathogenesis of various inflammatory-related diseases and therefore may serve as potential therapeutic targets. For example, elevated levels of some pro-inflammatory cytokines (TNF-α, IFNγ, IL-1, IL-2, IL-6 and IL-12) and chemokines (IL-8, MCP-1 and RANTES) have been observed in several inflammatory-related diseases such as CD, psoriasis, RA, Grave's disease and Hashimoto's thyroiditis (34), which parallels an increase in soluble TNF receptors, IL-1 receptor antagonists and the anti-inflammatory cytokine IL-10 (36, 37). IL-10 has been shown to suppress elevated pro-inflammatory cytokine production both in vitro in LPMC cultures and in vivo in patients (38). Positive response of CD patients treated with IL-10 demonstrates that there might also be an imbalance between the production of pro-inflammatory and anti-inflammatory cytokines in CD.

In summary, the approach of treating inflammatory-related diseases has undergone an evolutionary change in recent years in part as a consequence of growing concerns of the severity of these diseases and in part due to considerable progress in the understanding of the important role of cytokines in their immuno-pathogenesis. The majority of the efforts have been focused on targeting TNF-α and IL-1 (39), and several products (TNF-α inhibitors: infliximab, a monoclonal anti-TNF-α antibody; and etanercept, the p75 TNF-α receptor) are currently marketed or in clinical trials for the treatment of RA, psoriasis and IBD as mentioned above. Several other drug candidates or strategies targeting IL-1 (40), IL-6 or IL-10 are under development (40-42). These biological treatments provide significant efficacy in the short and medium term in many patients with RA (43-46). Although these drugs are well tolerated and have a good overall safety profile, active pharmaco-vigilance is needed. Based on its mechanism of action, and previous notifications of a wide variety of adverse effects, long-term risks of side effects including haematological, infectious, neurological, oncological and immunological effects need to be examined.

Strategies for targeting a single pro-inflammatory cytokine as an anti-inflammatory therapy ignore a very important fact, which is that inflammatory-related diseases involve a sophisticated cytokine network "system". For example, chemokines, a family of immune molecules related to IL-8 contains approximately 50 ligands and 20 receptors, often acting with redundancy, thus making selection of appropriate specific antagonists not only difficult, but lacking in long-term efficacy. In addition, currently marketed products or products under development are mainly protein-based agents, which are expensive to produce and inconvenient to administer (i.e., infusion). Therefore, as functioning of the immune system is finely balanced by the activities of pro-inflammatory and anti-inflammatory mediators or cytokines, modulation of multiple pro/anti-inflammatory cytokines instead of blocking only one particular pro-inflammatory cytokine by small molecules should not only achieve better therapeutic efficacy with less side effects, but will also have the many advantages of small molecule drugs.

Based on this concept, we examined several types of small molecules to test their ability in the regulation of multiple cytokines and explored their potential clinical applications for the treatment of a variety of inflammatory-related diseases.

Meisoindigo is an indirubin derivative that has been used for the treatment of chronic myeloid leukemia (CML) in China with minor side effects (47). In our previous patent (U.S. Pat. No. 6,566,341), we demonstrated that Meisoindigo and its derivatives are active against solid tumors through their ability to inhibit cyclin-dependent kinases, induce cell differentiation and promote apoptosis. In the current invention, we show novel therapeutic activities of this class of molecules in the treatment of various inflammatory-related diseases including inflammatory bowel diseases and psoriasis in rodents as well as in humans. We demonstrate that this type of agent inhibits the secretion and expression of multiple pro-inflammatory cytokines including IL-1, IL-6 and TNF-α in cell lines, and promotes production of anti-inflammatory cytokine IL-10. In one human case, Meisoindigo also proves very effective against IBD while no significant side effects were observed.

EP 1 079 826 to Eisenbrand et al., titled "Use of Indigoid Bisindole Derivatives for the Manufacture of a Medicament to Inhibit Cyclin Dependent Kinases," is directed to the use of indigoid bisindole derivatives for the manufacture of a medicament for the treatment of diseases associated with the loss of proliferation control. According to EP 1 079 826, psoriasis, cardiovascular diseases, infectious diseases, nephrology, neurodegenerative disorders and viral infections are all diseases associated with the loss of cell proliferation control. EP 1 079 826 teaches that the medicament is effective at treating theses diseases associated with the loss of proliferation control by inhibiting cyclin dependent kinases (CDKs).

In contrast, Applicants discovered that isoindigo, indigo, indirubin, and derivatives thereof can be used to suppress or inhibit expression pro-inflammatory cytokines, e.g., TNF-α, IL-1 and IL-6, to treat inflammatory-related diseases associated with cytokine expression.

While certain diseases mentioned in EP 1 079 826 as being associated with the loss of cell proliferation control are also related to cytokine expression, Applicants have found that the amount of therapeutic agent required to treat these corresponding diseases by inhibiting the cytokine levels is significantly less than that required to inhibit CDKs as taught by EP 1 079 826.

SUMMARY OF THE INVENTION

The present invention provides pharmaceutical compositions and methods of treating various inflammatory-related diseases associated with cytokine expression levels in animals using Meisoindigo and other derivatives of isoindigo, indigo and indirubin to inhibit expression of pro-inflammatory cytokines. These compositions and methods allow for the treatment of a variety of inflammatory-related diseases with minimal side effects. One of the most important advantages of the present invention is that the therapeutic compounds not only address symptoms of various inflammatory-related diseases, but also modify the diseases through suppression of expression/secretion of multiple pro-inflammatory cytokines (IL-1α, β, IL-2, IL-3, IL-6, IL-7, IL-9, IL-12, IL-17, IL-18, TNF-α, LT, LIF, Oncostatin, or IFNc1α, β, γ) and/or by stimulation of expression anti-inflammatory cytokines (IL-4, IL-10, IL-11, W-13 or TGFβ).

The present invention often results in a cure instead of simply a temporary remission of the disease symptoms. In contrast, the existing therapies for inflammatory-related diseases, in most cases, only relieve the symptoms for a short duration. Furthermore, the therapeutic compounds of the present invention are small molecules that are simple, chemically stable, and are substantially easy to produce and administer. Furthermore, Applicants have found that comparatively low dosages/concentrations of the compounds are generally sufficient to substantially inhibit the pro-inflammatory cytokines in the patient, reducing the risk of side effects associated with treatment.

The pharmaceutical compositions for treating an inflammatory-related disease described herein preferably include at least one compound of formula (I), (II), or (III)

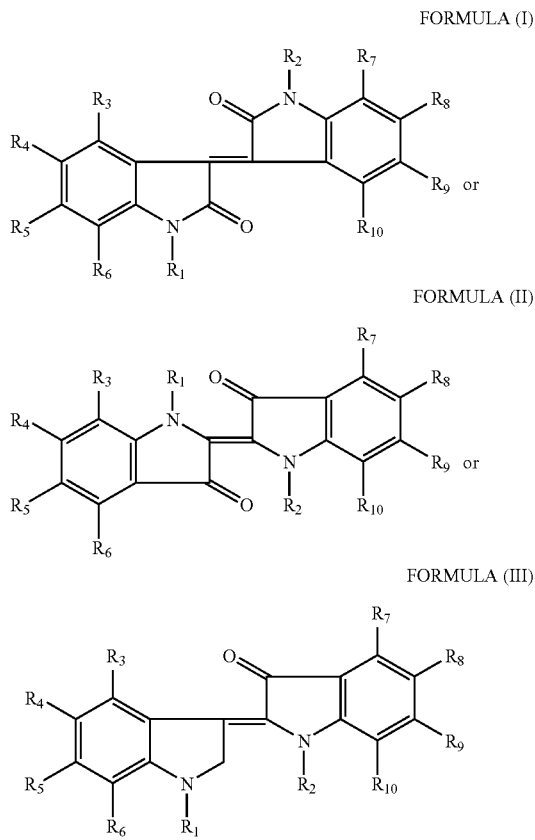

FORMULA (I)

FORMULA (II)

FORMULA (III)

wherein the compound is in an amount sufficient to treat the inflammatory-related disease by inhibiting pro-inflammatory cytokine expression or by stimulating anti-inflammatory cytokine expression, but the amount is less than sufficient to substantially inhibit cyclin dependent kinases;

$R_3$, $R_4$, $R_5$, $R_6$, $R_7$, $R_8$, $R_9$, and $R_{10}$ are the same or different and represent a hydrogen atom; a hydroxy group; a nitroso group; a nitro group; a monosaccharide; a disaccharide; a halogen atom; a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfates, sulfonates, sulfonamides or halogens, wherein the hydrocarbyl has 1 to 8 carbon atoms; a —$R_{11}R_{12}$ group, wherein $R_{11}$ and $R_{12}$ can be the same or different and represent a hydrogen atom, a straight-chain or branched-chain alkyl group having 1 to 18 carbon atoms which can additionally carry one or more hydroxy and/or amino groups, a substituted or unsubstituted aryl group which can comprise one or more heteroatoms, or an acyl group, or $R_{11}$ and $R_{12}$ form together a ring having 2 to 6, optionally substituted, $CH_2$ groups; an azo group —N=N—$R_{13}$, wherein $R_{13}$ represents an aromatic system which can be substituted by one or more carboxyl groups and/or phosphoryl groups, or a group selected from the group consisting of sugars, amino acids, peptides or steroid hormones; or $R_1$ and $R_6$, and $R_2$ and $R_7$, respectively, form independently from each other a ring together having 1 to 4, optionally substituted, $CH_2$ groups; and $R_1$ and $R_2$ are the same or different and represent a hydrogen atom; a halogen atom; a hydroxy group; a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfates, sulfonates, sulfonamides or halogens, wherein the hydrocarbyl has 1 to 8 carbon atoms; a mono-, di- or trialkylsilyl group having 1 to 6 carbon atoms independently of each other in each instance in the straight-chain or branched-chain alkyl group; a mono-, di- or triarylsilyl group with substituted or unsubstituted aryl groups independently of each other in each instance; a —$NR_{17}R_{18}$ group, wherein $R_{17}$ and $R_{18}$ can be the same or different and represent a hydrogen atom, a straight-chain or branched-chain alkyl group having 1 to 18 carbon atoms which can additionally carry one or more hydroxy and/or amino groups, a substituted or unsubstituted aryl group which can comprise one or more heteroatoms, or an acyl group; a methyleneamino group —$CH_2$—$NR_{17}R_{18}$, wherein $R_{17}$ and $R_{18}$ have the above definitions; a physiological amino acid residue bound to the nitrogen as an amide, substituted or unsubstituted monosaccharide, disaccharides or oligosaccharides; or a sugar, amino acid, peptide or steroid hormone.

Preferably, at least $R_1$ or $R_2$ is a monosaccharide, a disaccharide unsubstituted or substituted with one or more hydroxy moieties or carboxy moieties; a halogen; a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfates, sulfonates, sulfonamides or halogens, wherein the hydrocarbyl has 1 to 8 carbon atoms.

In another embodiment at least $R_1$ or $R_2$ is an acetylated monosaccharide. Preferably, at least $R_1$ or $R_2$ can be a methyl group.

Preferred compounds include: Meisoindigo, tri-acetylated glyco-Meisoindigo (pro-drug) or NATURA, shown as Formulas (IV), (V), and (VI) respectively:.

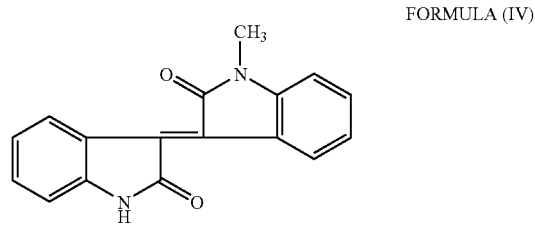

FORMULA (IV)

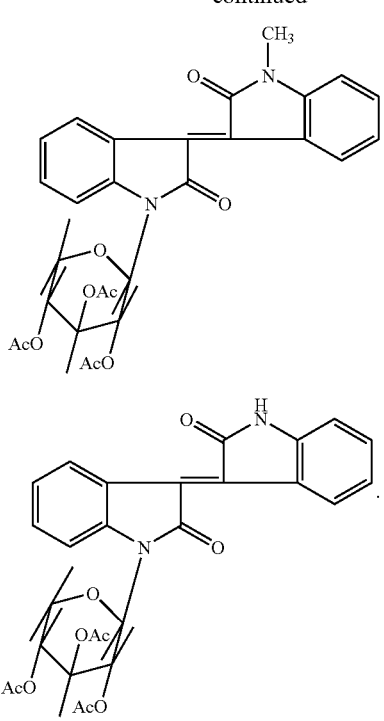

FORMULA (V)

FORMULA (VI)

The pharmaceutical composition also typically also comprises a pharmaceutically acceptable carrier. Preferably the carrier is an inert diluent.

In one embodiment the pharmaceutical composition also comprises an anti-inflammatory agent. Preferably the anti-inflammatory agent is selected from the group consisting of: an analgesic; an antirheumatic agent; an gastrointestinal agent; a gout preparation; glucocorticoids; opthalmic preparation; respiratory agent; a nasal preparation; and a mucous membrane agent.

When an analgesic is included, preferably it is selected from the group consisting of: naproxen, indomethacin, ibuprofen, ketorolac tromethamine, choline magnesium trisalicylate and rofecoxib; the antirheumatic agent is selected from the group consisting of: cyclosporine, sulfasalazine, valdecoxib, penicillamine and dexamethasone; the gastrointestinal agent is selected from the group consisting of: mesalamine, balsalazide disodium and olsalazine sodium; the gout preparation is sulindac; the glucocorticoid is selected from the group consisting of: dexamethasone, dexamethasone phosphate, methylprednisolone acetate, hydrocortisone and hydrocortisone sodium phosphate; the nasal preparation is selected form the group consisting of beclomethasone dipropionate monohydrate, fluticasone propionate, triamcinolone acetonide, flunisolide, mometasone furoate monohydrate and budesonide; the opthalmic preparation is ketorolac tromethamine; the respiratory agent is nedocromil sodium; and the mucous membrane agent is selected from the group consisting of: alclometasone dipropionate, hydrocortisone butyrate, flurandrenolide, betamethasone valerate and clobetasol propionate.

DETAILED DESCRIPTION OF THE PREFERRED EMBODIMENTS

Figure 1:
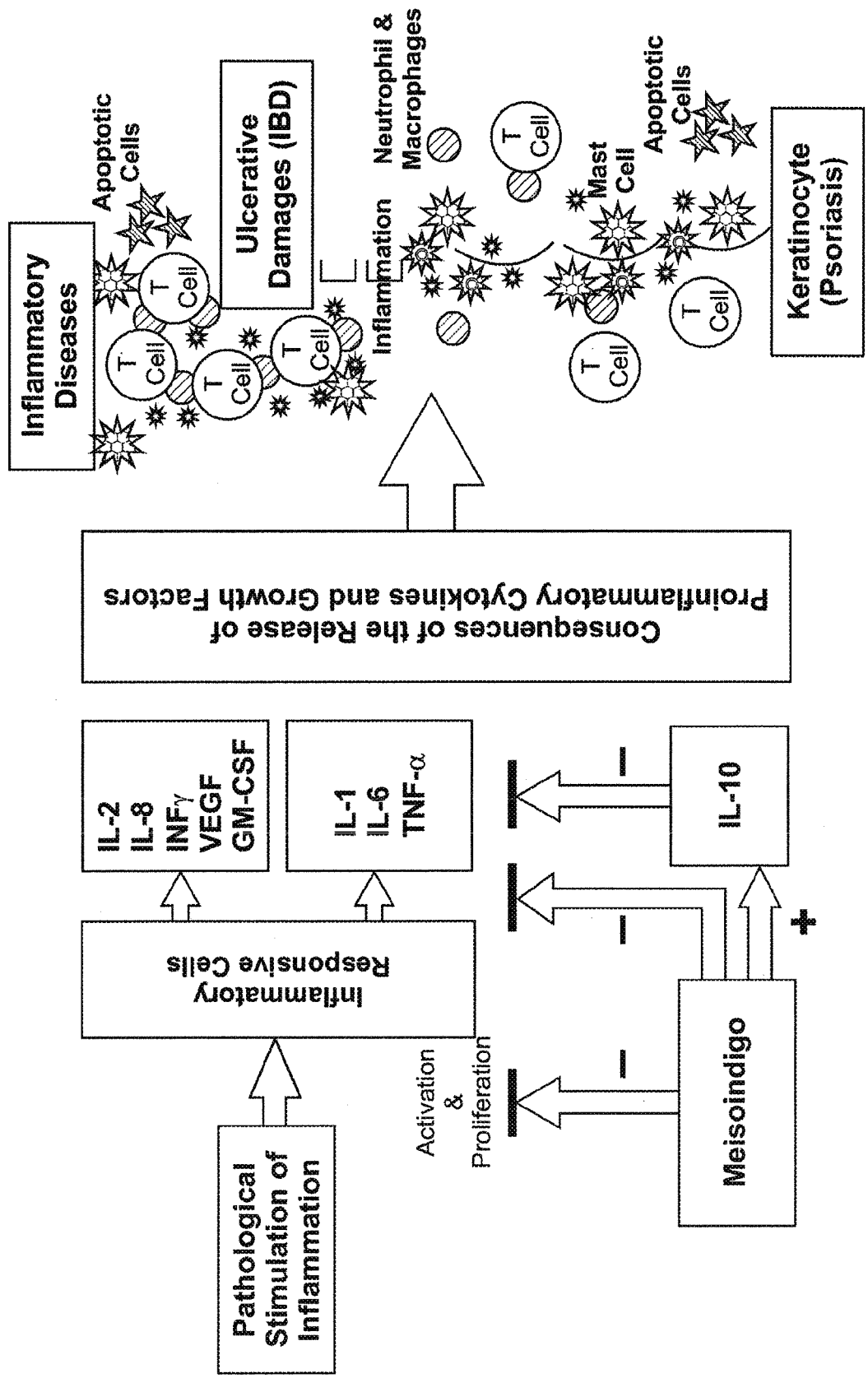
FIG. 1 is a schematic representation of roles of pro-/anti-inflammatory cytokines and growth factors, and action sites of Meisoindigo in the pathological process of chronic inflammatory-related diseases.

The present invention is directed to pharmaceutical compositions and methods of treating inflammatory-related diseases associated diseases associated with pro-inflammatory cytokine expression and/or reduced anti-inflammatory expression. A preferred method of the present invention comprises administering to an animal in need of such treatment one or more compound selected from the group consisting of isoindigo, indigo, indirubin, or derivatives thereof. In a preferred embodiment, the compound being administered is in an amount sufficient to treat the inflammatory-related disease by inhibiting pro-inflammatory cytokine expression and/or by stimulating anti-inflammatory cytokines, but less than sufficient to substantially inhibit cyclin dependent kinases (CDKs).

As used herein, "to substantially inhibit CDKs" means a concentration sufficient to inhibit 30%, more preferably 40%, and most preferably a concentration equal to or higher than the inhibitory concentration 50% ($IC_{50}$) for CDKs. The CDK that is inhibited is preferably one or more CDK selected from the group consisting of CDK1, CDK2, CDK4 CDK5, and CDK6.

It should be understood that the present methods includes, but is not limited to, treating the inflammatory-related disease by preventing inflammation associated with the disease by regulating cytokines involved in the pathological progress, thus preventing the onset the inflammatory-related disease.

The inflammatory-related disease is preferably selected from the group consisting of: arthritis, rheumatoid arthritis, an inflammatory bowel disease; psoriasis; multiple sclerosis; a neurodegenerative disorder; congestive heart failure; stroke; aortic valve stenosis; kidney failure; lupus; pancreatitis; allergy; fibrosis; anemia; atherosclerosis; a metabolic disease; a bone disease; a cardiovascular disease, a chemotherapy/radiation related complication; diabetes type I; diabetes type II; a liver disease; a gastrointestinal disorder; an ophthamological disease; allergic conjunctivitis; diabetic retinopathy; Sjogren's syndrome; uveitis; a pulmonary disorder, a renal disease; dermatitis; HIV-related cachexia; cerebral malaria; ankylosing spondolytis; leprosy; anemia; and fibromyalgia.

Preferably the neurodegenerative disorder is selected from the group consisting of: Alzheimer's disease and Parkinson disease; the inflammatory bowel disease is selected from the group consisting of: Crohn's disease or uncerative colitis; the gastrointestinal complication is diarrhea; the liver disease is selected from the group consisting of: an autoimmune hepatitis, hepatitis C, primary biliary cirrhosis, primary sclerosing cholangitis, or fulminant liver failure; the gastrointestinal disorder is selected from the group consisting of: celiac disease and non-specific colitis; the bone disease is osteoporosis; the pulmonary disorder is selected from the group consisting of: allergic rihinitis, asthma, chronic obstructive pulmonary disease, chronic granulomatous inflammation, cystic fibrosis, and sarcoidosis; the cardiovascular disease is selected from the group consisting of: atheroscleotic cardiac disease, congestive heart failure and restenosis; and the renal disease is selected from the group consisting of: glomerulpnephritis and vasculitis.

In a preferred embodiment the disease is inflammatory bowel disease (IBD), specifically including Crohn's disease and uncerative colitis. In another preferred embodiment the disease being treated is arthritis, rheumatoid arthritis, psoriasis, Alzheimer's disease, or Parkinson disease. In yet another preferred embodiment the disease is post-radiotherapy related disease or atherosclerosis.

Preferably the compound is in an amount to inhibit pro-inflammatory cytokine expression and/or to stimulate anti-inflammatory cytokine expression. In one embodiment, the compound is preferably in an amount to inhibit at least 30% expression of one or more of the pro-inflammatory cytokines selected from the group consisting of: IL-1α, β, IL-2, IL-3, IL-6, IL-7, IL-9, IL-12, IL-17, IL-18, TNF-α, LT, LIF, Oncostatin, and IFNc1α, β, γ: More preferably at least 40% expression of the cytokine is inhibited and most preferably 50% or more is inhibited. In another embodiment, the compound is preferably in an amount to stimulate anti-inflammatory cytokine expression. In this embodiment, the compound is preferably in an amount to increase the anti-inflammatory cytokine selected from the group consisting of: cytokine IL-4, IL-10, IL-11, W-13 or TGFβ by at least 25%, more preferably at least 50%, and most preferably at least 75%.

Chemical Structures

The present invention is directed a pharmaceutical composition for treating an inflammatory-related disease comprising at least one compound selected from a specific group that includes isoindigo, indigo, indirubin and derivatives thereof. Preferably, the compounds are selected from Formulas (I), (II) and (III)

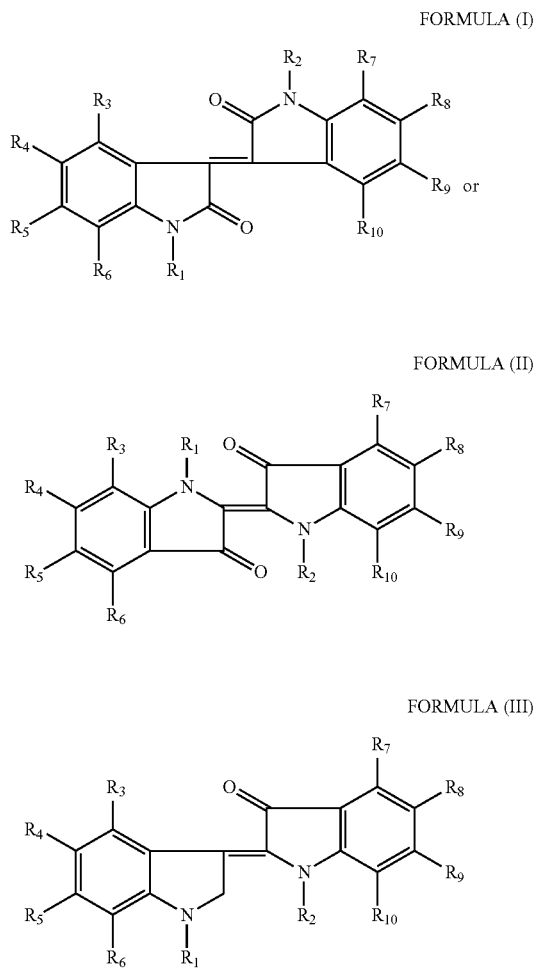

FORMULA (I)

FORMULA (II)

FORMULA (III)

wherein $R_3$, $R_4$, $R_5$, $R_6$, $R_7$, $R_8$, $R_9$, and $R_{10}$ are the same or different and represent a hydrogen atom; a hydroxy group; a nitroso group; a nitro group; a monosaccharide; a disaccharide; a halogen atom; a hydrocarbyl group; or a functional hydrocarbyl group unsubstituted or substituted with one or more hydroxy moieties, carboxy moieties, nitroxy moieties, monosaccharides, disaccharides, amines, amides, thiols, sulfates, sulfonates, sulfonamides or halogens, wherein the hydrocarbyl has 1 to 8 carbon atoms; a —$R_{11}R_{12}$ group, wherein $R_{11}$ and $R_{12}$ can be the same or different and represent a hydrogen atom, a straight-chain or branched-chain alkyl group having 1 to 18 carbon atoms which can additionally carry one or more hydroxy and/or amino groups, a substituted or unsubstituted aryl group which can comprise one or more heteroatoms, or an acyl group, or $R_{11}$ and $R_{12}$ form together a ring having 2 to 6, optionally substituted, $CH_2$ groups; an azo group —N═N—$R_{13}$, wherein $R_{13}$ represents an aromatic system which can be substituted by one or more carboxyl groups and/or phosphoryl groups, or a group selected from the group consisting of sugars, amino acids, peptides or steroid hormones; or $R_1$ and $R_6$, and $R_2$ and $R_7$, respectively, form independently from each other a ring together having 1 to 4, optionally substituted, $CH_2$ groups;

The groups $R_1$ and $R_2$ are the same or different and represent a hydrogen atom; a halogen atom; a hydroxy group; a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfates, sulfonates, sulfonamides or halogens, wherein the hydrocarbyl has 1 to 8 carbon atoms; a mono-, di- or trialkylsilyl group having 1 to 6 carbon atoms independently of each other in each instance in the straight-chain or branched-chain alkyl group; a mono-, di- or triarylsilyl group with substituted or unsubstituted aryl groups independently of each other in each instance; a —$NR_{17}R_{18}$ group, wherein $R_{17}$ and $R_{18}$ can be the same or different and represent a hydrogen atom, a straight-chain or branched-chain alkyl group having 1 to 18 carbon atoms which can additionally carry one or more hydroxy and/or amino groups, a substituted or unsubstituted aryl group which can comprise one or more heteroatoms, or an acyl group; a methyleneamino group —$CH_{17}R_{18}$, wherein $R_{17}$ and $R_{18}$ have the above definitions; a physiological amino acid residue bound to the nitrogen as an amide, substituted or unsubstituted monosaccharide, disaccharides or oligosaccharides; or a sugar, amino acid, peptide or steroid hormone.

Preferred compounds are those in which at least one $R_1$, $R_2$, $R_3$, $R_4$, $R_5$, $R_6$, $R_7$, $R_8$, $R_9$, or $R_{10}$ is independently a monosaccharide, a disaccharide, or a hydrocarbyl group or a functional hydrocarbyl group substituted with one or more hydroxy moieties, carboxy moieties, nitroxy moieties, monosaccharides, disaccharides, amines, amides, thiols, or halogens, wherein the hydrocarbyl has 1 to 8 carbon atoms; and at least one of $R_1$, $R_2$, $R_3$, $R_5$, $R_6$, $R_7$, $R_8$, $R_9$, or $R_{10}$ enhances the bioactivity or bioavailability of the compound.

It is preferable that $R_1$, $R_2$, $R_3$, , $R_5$, $R_6$, $R_7$, $R_8$, $R_9$, or $R_{10}$ enhances the bioactivity or bioavailability of the compound by increasing the solubility of the compound. It is more preferable that both the bioactivity and bioavailability are increased by one or more of $R_1$, $R_2$, $R_3$, $R_4$, $R_5$, $R_6$, $R_7$, $R_8$, $R_9$, or $R_{10}$.

Preferred compounds are those in which at least $R_1$ or $R_2$ is a monosaccharide; a disaccharide unsubstituted or substituted with one or more hydroxy moieties or carboxy moieties; a halogen; a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfates, sulfonates, sulfonamides or halogens, wherein the hydrocarbyl has 1 to 8 carbon atoms. In many cases only one of $R_1$ or $R_2$ needs to be one of the recited moieties, with one of the most preferred substituents being —$CH_2CH_2OH$.

More Preferred compounds of Formulas (I), (II), and (III) are ones in which $R_1$ or $R_2$ is a glycoside molecule, most preferably a monosaccharide, and most preferably an acetylated monosaccharide. In a preferred embodiment the glycoside molecule is selected from an acetylated arabinose, glucose, mannose, ribose or xylose molecule.

In one embodiment of the invention the compounds are Meisoindigo, tri-acetylated glyco-Meisoindigo (pro-drug) and NATURA, shown as Formulas (IV), (V), and (VI) respectively.

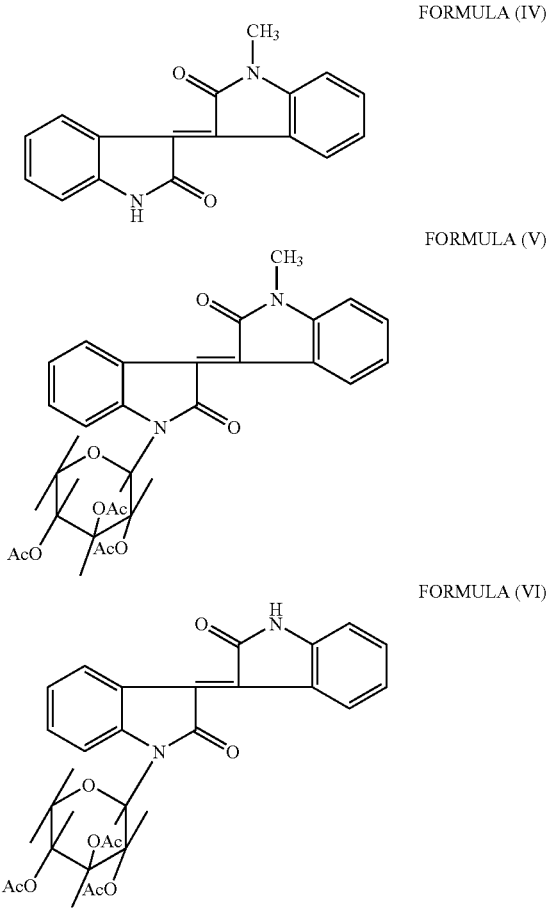

FORMULA (IV)

FORMULA (V)

FORMULA (VI)

The examples given below are simply to demonstrate different embodiments of the invention and are not intended in any way to limit the scope of the present invention thereto.

The term "hydrocarbyl" in the context of the present invention, and in the above formulas, broadly refers to a monovalent hydrocarbon group in which the valency is derived by abstraction of a hydrogen from a carbon atom. Hydrocarbyl includes, for example, aliphatics (straight and branched chain), cycloaliphatics, aromatics and mixed character groups (e.g., aralkyl and alkaryl). Hydrocarbyl also includes such groups with internal unsaturation and activated unsaturation. More specifically, hydrocarbyl includes (but is not limited to) such groups as alkyl, cycloalkyl, aryl, aralkyl, alkaryl, alkenyl, cycloalkenyl and alkynyl, preferably having up to 12 carbon atoms. The preferred embodiments include those in which the hydrobcarbyl group has 1 to 8 carbon atoms. These and other hydrocarbyl groups may optionally contain a carbonyl group or groups (which is/are included in the carbon count) and/or a heteroatom or heteroatoms (such as at least one oxygen, sulfur, nitrogen or silicon), in the chain or ring.

The term "functional hydrocarbyl" in the context of the present invention, and in the above formulas, broadly refers to a hydrocarbyl possessing pendant and/or terminal "reactive" and/or "latent reactive" functionalities and/or leaving groups. Reactive functionalities refer to functionalities, which are reactive with common monomer/polymer functionalities under normal conditions well understood by those persons of ordinary skill in the relevant art. Examples of reactive functionalities are active hydrogen containing groups such as hydroxyl, amino, carboxyl, thio, amido, carbamoyl and activated methylene; isocyanato, cyano and epoxy groups; ethylenically unsaturated groups such as allyl and methallyl; and activated unsaturated groups such as acryloyl and methacryloyl, and maleate and maleimido (including the Diels-Alder adducts thereof with dienes such as butadiene). Latent reactive functionalities within the meaning of the present invention and, as would clearly be understood by those persons of ordinary skill in the relevant art, refers to reactive functionalities which are blocked or masked to prevent premature reaction. Examples of latent reactive functionalities are ketimines and aldimines (amines blocked, respectively, with ketones and aldehydes); amine-carboxylate salts; and blocked isocyanates such as alcohol (carbamates), oxime and caprolactam blocked variations. A "leaving" group within the meaning of the present invention and, as would clearly be understood by those persons of ordinary skill in the relevant art, is a substituent attached to the hydrocarbyl chain or ring which during reaction is displaced to create a valency on a carbon or hetero atom in the hydrocarbyl chain or ring. Examples of leaving groups are halogen atoms such as chlorine, bromine and iodine; quaternary ammonium salts; sulfonium salts; and sulfonates.

A monosaccharide or disaccharide of the present invention is preferably glucose, fructose, ribulose, galactose, mannose, cellobiose, allose, altrose, ribose, xylose, arabinose, sucrose, or lactose. Most preferably it is D-glucose, D-ribose, D-galactose, D-lactose, D-xylose or D-sucrose.

In one preferred embodiment the monosaccharide or disaccharide is acetylated, preferably at least di-acetylated and more preferably tri-acetylated.

The term "halogen" indicates fluorine, chlorine, bromine, or iodine. Preferably it is fluorine or chlorine.

As used herein, amino acid means an L- or D-amino acid (or a residue thereof), preferably L-, selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine. The term peptide is two or more amino acids joined by a peptide bond, preferably containing 2 to 8 amino acids, and more preferably containing 2 to 6 amino acids.

Pharmaceutical Preparations and Administrations

The invention may be used to treat an animal with an inflammatory-related disease, wherein it is preferable that the animal is a mammal and more preferable that the animal is a human.

It should also be noted that therapeutic benefits typically are realized by the administration of at least 1, 2, 3 or more of the compounds concurrently or sequentially. The compounds of the invention may also be combined with other therapies to provide combined therapeutically effective amounts. The compound can be administered, for example, in combination with additional agents, preferably anti-inflammatory agents.

In a preferred embodiment, the pharmaceutical composition for treating an inflammatory-related disease associated with pro-inflammatory cytokine expression includes one or more compounds selected from isoindigo, indigo, indirubin, or a derivative thereof as described above; an anti-inflammatory agent, and a pharmaceutically acceptable carrier, wherein the anti-inflammatory agent is selected from the group consisting of: an analgesic; an antirheumatic agent; an gastrointestinal agent; a gout preparation; glucocorticoids; opthalmic preparation; respiratory agent; a nasal preparation; and a mucous membrane agent.

Preferably the analgesic is selected from the group consisting of: naproxen, indomethacin, ibuprofen, ketorolac tromethamine, choline magnesium trisalicylate and rofecoxib; the antirheumatic agent is selected from the group consisting of: cyclosporine, sulfasalazine, valdecoxib, penicillamine and dexamethasone; the gastrointestinal agent is selected from the group consisting of: mesalamine, balsalazide disodium and olsalazine sodium; the gout preparation is sulindac; the glucocorticoid is selected from the group consisting of: dexamethasone, dexamethasone phosphate, methylprednisolone acetate, hydrocortisone and hydrocortisone sodium phosphate; the nasal preparation is selected form the group consisting of beclomethasone dipropionate monohydrate, fluticasone propionate, triamcinolone acetonide, flunisolide, mometasone furoate monohydrate and budesonide; the opthalmic preparation is ketorolac tromethamine; the respiratory agent is nedocromil sodium; and the mucous membrane agent is selected from the group consisting of: alclometasone dipropionate, hydrocortisone butyrate, flurandrenolide, betamethasone valerate and clobetasol propionate.

In another preferred embodiment pharmaceutical composition comprises meisoindigo and/or NATURA. Typically the pharmaceutically acceptable carrier is an inert diluent.

Furthermore, in yet another embodiment the compound—isoindigo, indigo, indirubin, or a derivative thereof—is in an amount sufficient to treat the inflammatory-related disease by inhibiting pro-inflammatory cytokine expression and/or by stimulating anti-inflammatory cytokine expression, but less than sufficient to substantially inhibit cyclin dependent kinases. In this embodiment, the additional anti-inflammatory agent mentioned above is not required in the composition to be effective, but is advantageous.

The pharmaceutical compositions of the invention can take a variety of forms adapted to the chosen route of administration as discussed above. Those skilled in the art will recognize various synthetic methodologies that may be employed to prepare non-toxic pharmaceutically acceptable compositions of the compounds described herein. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compositions of the invention may be administered orally, topically, parenterally, by inhalation or spray or rectally in dosage unit formulations containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques.

The pharmaceutical compositions containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a single dosage form will vary depending upon the condition begin treated and the particular mode of administration. Dosage unit forms will generally contain between from about 1 mg to about 500 mg of an active ingredient. The dosage will preferably be at least three times less for treating inflammatory diseases via cytokine modulation than that for treating proliferative disorders by inhibiting CDKs. For example, a dosage of Meisoindigo to treat CML is generally about 125 mg per day, while the dosage of Meisoindigo to treat IBD is typically only 25 mg per day. This is due to the significant lower amount needed for the regulation of cytokines by this class of molecules, than required to regulate CDKs.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

The amount of the composition required for use in treatment will vary not only with the particular compound selected but also with the route of administration, the nature of the condition being treated and the age and condition of the patient and will ultimately be at the discretion of the attendant physician or clinician.

Therapeutic Indications of Meisoindigo and Other Derivatives of Isoindigo, Indigo and Indirubin This invention provides a method of using a class of small molecules, Meisoindigo and derivatives of isoindigo, indigo and indirubin for the treatment of various inflammatory-related diseases in animals. These inflammatory-related diseases include, but are not limited to inflammatory bowel diseases (IBD), psoriasis, rheumatoid arthritis (RA), multiple sclerosis (MS), neurodegenerative disorders, cardiovascular disease (CVD) and atherosclerosis, and metabolic disease (the metabolic syndrome and diabetes,) as well as infection-related inflammation.

In the past 10 years, the development of inhibitors of TNF-$\alpha$ and other cytokines has been one of the most active areas of drug development for the treatment of various inflammatory-related diseases. Although short periods of clinical results applying those specific inhibitors for the treatment of various inflammatory-related diseases are positive and even exciting, and the future development of anti-TNF-$\alpha$ and anti-cytokine therapy in general will be interesting (34), the long term effectiveness of these treatments has been challenged by the fact that not only a single pathway but a complicated cytokine network system is involved in the pathological process of inflammatory-related diseases.

Pro-inflammatory cytokines have been implicated in a wide range of pathological inflammatory processes, as has reduced expression of anti-inflammatory cytokines.

FIG. 1 shows the schematic representation of pathological processes in human inflammatory-related diseases that involve various cytokines and growth factors providing a schematic representation of roles of pro-/anti-inflammatory cytokines and growth factors, and action sites of derivatives such as Meisoindigo in the pathological process of chronic inflammatory-related diseases: Pathological stimulation of inflammation triggers inflammatory responsive cells (lymphocytes, monocytes, neutrophils, endothelial cells, tissue macrophages and mast cells) to release pro-inflammatory cytokines and growth factors. These pro-inflammatory cytokines and growth factors in turn, lead to the egress of immune cells, neutrophils and blood monocytes from the blood supply and their subsequent accumulation at the sites of inflammation. These consequently cause various inflammatory-related diseases, and/or autoimmune disorders. These diseases include, inflammatory bowel disease (IBD), psoriasis, Rheumatoid arthritis, neuro-degeneration, and others. Meisoindigo, at low concentrations (e.g., 30 nM) inhibits production of multiple pro-inflammatory cytokines including IL-1β, IL-6, and TNF-α, and stimulates anti-inflammatory cytokine IL-10.

Table 1 summarizes the involvement of various cytokines in the pathological process of autoimmune disorders. While significant increases in various pro-inflammatory cytokines are found in the tissues/organs of autoimmunological diseases, some regulatory cytokines are moderately elevated to balance the over-activated pro-inflammatory cytokines. It is also believed autoimmune disorders are caused by an imbalance between the pro-inflammatory and the regulatory cytokines (48).

On the basis of our observations in this invention showing that Meisoindigo down regulates the secretion/expression of several major pro-inflammatory cytokines: TNF-α, IL-1 and IL-6 and up regulates anti-inflammatory cytokines IL-10. The term "consequences of the release of pro-inflammatory cytokines and growth factors" refers to epidermotropism of T cells, induction of K6/16 hyperproliferation, lining macrophages, infiltration of activated newtrophils and T cells, mast cell increase and activation, induction of ICAM-1 and MHC class II, angiogenesis, change in vascular permeability, apoptosis, damage to the brain and central nervous system, regulation of synovial cell proliferation, cartilage degradation and bone resorption.

TABLE 1

List of cytokines and growth factors involved in the pathological process of various inflammatory disorders

| Pro-inflammatory Cytokines | Regulatory Cytokines | Chemokines | Growth Factors |
|---|---|---|---|
| TNF-α | IL-4 | IL-8 | FGF |
| LT | IL-10 | Groα | PDGF |
| LIF | IL-11 | MIP-1 | VEGF |
| Oncostatin M | W-13 | MCP-1 | GM-CSF |
| W-15 | | ENA-78 | M-CSF |
| IFNc1α/β | | RANTES | TGF-β |
| IFNγ | | | |
| IL-1α, β | | | |
| IL-2 | | | |
| IL-3 | | | |
| IL-6 | | | |
| IL-7 | | | |
| IL-9 | | | |
| IL-12 | | | |
| IL-17 | | | |
| IL-18 | | | |

Inflammatory Bowel Disease (IBD): IBD comprises Crohn's disease (CD) and ulcerative colitis (UC), which are 2 overlapping chronic inflammatory-related diseases of the gastrointestinal tract caused by dysregulation of the immune system (20). Patients with IBD have defective intestinal epithelial barrier function, which allows bacterial colonization of the epithelia. As a result, bacterial products and pro-inflammatory cytokines (TNF-α, IL-1 and IL-6) cause persistent inflammatory stimulation. Bacterial antigens are introduced into the immune system by mucosal dendritic cells and macrophases. In response, intestinal phagocytes (mainly monocytes and neutrophils) proliferate and increase expression and secretion of pro-inflammatory cytokines. As the cell growth inhibitors and cell differentiation inducers demonstrated in our previous patent, Meisoindigo and derivatives of isoindigo, indigo and indirubin will effectively inhibit the overactive proliferation of those inflammatory cells while suppressing their expression/secretion of pro-inflammatory cytokines as demonstrated in Examples 1 to 4. This conclusion has been confirmed in animal models as well as in a patient with IBD as shown in Examples 7-8.

Psoriasis: Cytokines are intercellular messengers that have an important role in the development and maintenance of cutaneous inflammation. A number of cytokines have been reported to play crucial roles in the pathogenesis of inflammatory skin disorders. IL-1, TNF-α, and IFN-γ induce expression of ICAM-1 and major histocompatibility complex (MHC) class II (48, 49). IL-1, TNF-α, and granulocyte-macrophage colony-stimulation factor are able to induce activation, maturation, and migration of dendritic cells, and IL-1 activates mast cells (50). IL-6 and TGF-α enhance keratinocyte proliferation. IL-1, TNF-α, TGF-α, and VEGF induce angiogenesis and attract inflammatory cells (51-53). The primacy of cytokines in eliciting cutaneous immune responses makes them a highly attractive target for new biological response modifiers (18). Therefore, as multi-cytokines regulators, the small molecules claimed in this invention, Meisoindigo and derivatives of isoindigo, indigo and indirubin will be effective against psoriasis.

Rheumatoid arthritis (RA): The role of the cytokine network in mediating inflammation and joint destruction in RA has been extensively investigated in recent years. In addition to TNF-α, IL-1 plays a pivotal role in the pathogenesis and the clinical manifestations of RA (54). The ability of IL-1 to drive inflammation and joint erosion and to inhibit tissue repair processes has been clearly established in in vitro systems and in animal models, and alleviation of inflammatory symptoms in RA patients has been achieved by blockage of IL-1 (55). IL-6 is a multifunctional cytokine that regulates the immune response, hematopoiesis, the acute phase response, and inflammation. Deregulation of IL-6 production is implicated in the pathology of several diseases including RA. A therapeutic approach to block the IL-6 signal has been carried out by using humanized anti-IL-6R antibody for RA among other diseases (11, 56). IL-10 is an anti-inflammatory cytokine. Expressing IL-10 has been shown to prevent arthritis or ameliorate the disease in animal models (57, 58). While it is obvious that cytokines such as TNF-α, IL-1, IL-6 and IL-10 have independent roles, they act in concert in mediating certain pathophysiological processes in RA. The finding of a class of molecules described in this invention, which are able to modulate these different cytokines, will result in dramatic therapeutic progress in the treatment of RA.

Multiple Sclerosis (MS): MS is an autoimmune inflammatory disorder. Although the cause of the body attacking its own myelin in MS patients remains unclear, deregulated cytokines are clearly involved in the process of the disease.

Using experimental autoimmune encephalomyelitis (EAE), a widely used model for studies of MS based on autoimmune, histopathological, genetic and clinical similarities, it has been shown that in the early active stage, both EAE and MS are characterized by the presence of perivascular inflammatory cuffs disseminated in the CNS, a process in which chemoattractant cytokines (chemokines) play an important role. There is evidence that the expression of chemokines (IL-8 family members) during CNS autoimmune inflammation is regulated by some pro-inflammatory cytokines, such as TNF (59). The roles of other pro-/anti-inflammatory cytokines such as IL-1β, IL-6 and IL-10 were also confirmed in EAE animal models (60-62) as well as in humans (63). IL-1β is present in MS lesions. IL-1 receptor antagonist (IL-1Ra) moderates the induction of experimental autoimmune encephalomyelitis (EAE). Increased risk of MS has been seen in individuals with High IL-1 (3 over IL-1Ra production ratio and high TNF over IL-10 production ratio (63).

Neurodegenerative disorders: Alzheimer's disease (AD) and Parkinson's disease (PK) are the 2 most common neurodegenerative disorders related to neuroinflammation. Neuroinflammation is a characteristic of pathologically affected tissue in several neurodegenerative disorders. These changes are particularly observed in affected brain areas of AD cases (64). The role of cytokines has been implicated in the pathogenesis of AD, although the mechanism by which cytokines contribute to the pathogenesis is not fully understood. In AD, microglia, especially those associated with amyloid deposits, have a phenotype that is consistent with a state of activation, including immunoreactivity with antibodies to class II major histocompatibility antigens and to inflammatory cytokines, IL-1β and TNF-α (65). One of the major neuropathological characteristics of AD is the brain deposition of senile plaques that are mainly composed of toxic amyloid beta-peptide (Abeta), which is generated from a family of Abeta containing precursor proteins (AbetaPP). Cytokines have been shown to stimulate gene expression of transcription of AbetaPP (66). Analysis of genetic linkage of loci controlling age-at-onset in AD and PK revealed a significant association of AD with glutathione S-transferase, omega-1 and 2 (GSTO1, GSTO2) genes (7). The function of GSTO1 appears related to the post-translational processing of pro-inflammatory cytokine IL-1β (67).

Post-radiotherapy related Inflammation: Radiation damage related inflammatory diseases to the rectum and sigmoid colon are most common complications with radiation therapy for cancers in the pelvic region, which include cancers of the cervix, uterus, prostate, bladder, and testes. Radiation proctosigmoiditis is the most common clinically apparent form of colonic damage after pelvic irradiation with an incidence of 5% to 20%. Patients typically exhibit symptoms of tenesmus, bleeding, low-volume diarrhea, and rectal pain. Rarely, low-grade obstruction or fistulous tracts into adjacent organs may develop.

The mechanism of radiation therapy is through its damage to DNA in actively proliferating cells. The pathological damages after localized radiation therapy to the intestine/colon can be divided into acute and chronic phases. The initial pathological changes include a loss of lymphocytes in the lamina propria and microscopic damage to mucosal epithelial cells and vascular endothelial cells. These changes manifest as villous blunting and a decrease in crypt regenerative cells and are followed by marked submucosal edema with increase of vascular permeability.

Progressive endarteritis appears to be the major mechanism by which the chronic effects occur, which later manifest as progressive fibrosis leading to mucosal atrophy, stricture formation, and thrombosis, causing secondary ischemic damage. Radiation colitis in the chronic phase demonstrates a very significant crypt distortion, vascular telangiectasia, and fibrosis of the lamina propria. Interestingly, some of these pathological changes are also present in long-standing IBD (68).

Thus, cytokines may play a key role among various gastrointestinal diseases in which inflammation exhibits a significant part. Recent studies have focused on the crucial role of cytokines in chronic IBD (69-74). To elucidate the role of cytokines in radiation proctitis, Indaram et al. (75) examined the colonic mucosal cytokine levels in patients with radiation proctitis and compared these values with those obtained from normal controls and patients with IBD. They found that the mucosal levels of IL-2, IL-6, and IL-8 were significantly higher and statistically significant (p<0.05) in both diseased (5.62±0.13, 1.60±0.31, 21.45±4.03 pg/mg) and normal-appearing mucosa (3.83±0.78, 1.36±0.34, 13.45±3.18 pg/mg) in the radiation proctitis group, compared with those of normal controls (1.74±0.23, 0.67±0.05, 4.99±1.39 pg/mg).

Thus, these findings demonstrate a similar activation of cytokines in patients with radiation proctitis and IBD. In the radiation proctitis patients it was demonstrated that IL-2, IL-6, and IL-8 levels in the mucosa were significantly greater compared to normal controls. In comparison, the IBD (UC and CD) patients demonstrated significantly higher levels of the cytokines including IL-1, IL-2, IL-6, and IL-8 compared to the normal controls.

The similarity in mucosal cytokine expression in these 2 diseases plausibly relates directly to the intense inflammatory nature of the diseases. It has been postulated that this similarity in cytokine activation in these 2 diseases may translate into the similar pathological changes seen in chronic IBD and radiation proctitis. This hypothesis is supported by that fact that the medical management of radiation proctitis, albeit rather unsatisfactorily, includes treatment with various aminosalicylic acid derivatives and corticosteroids given orally or topically. These treatment options are identical to the management of IBD.

As demonstrated in the present invention that Meisoindigo and its class of small molecules are capable of down-regulation of IL-β1, IL-6 and TNF-α, and up-regulation of regulatory cytokine IL-10, high efficacy and low side effects for this treatment are to be expected.

Other Cytokine Deregulation Related Diseases: Cardiovascular disease (CVD), atherosclerosis, and metabolic disease (the metabolic syndrome) also have been linked to the improper secretion/expression of pro/anti-inflammatory cytokines (10, 12-14, 76).

Diabetes: A fundamental defect in type II diabetes is insulin resistance, by which insulin fails to suppress glucose production from the liver and to promote consumption by peripheral tissues, resulting in hyperglycemia. Pancreatic β cells respond to excess plasma glucose by secreting more insulin to overcome the effects of insulin resistance. As insulin resistance progresses and the β cells are no longer able to meet the requirement for increasing amount of insulin secretion, plasma glucose levels increase and type II diabetes develops.

Many factors may contribute to the onset of type II diabetes. Since 80% of the patients with type II diabetes are obese and obesity is always associated with insulin resistance, molecular mediators that link obesity to insulin resistance have been under extensive research. A variety of factors have been identified as contributing causes of insulin resistance in obesity and obesity-linked type II diabetes, notable those produced by adipose tissue, FFAs (free fatty acids), TNFα, IL-6, leptin, adiponectin, and resistin. Both mRNA and protein levels of TNFα are highly increased in the adipose tissues of obese animals (77) and human subjects (78). All different types of cell in the adipose tissue are capable of producing cytokines. Adipocytes express TNFα receptors and are also the major source of TNFα, which is thought to function predominantly in an autocrine/paracrine manner in adipose tissue.

Long-term exposure of cultured cells (79) or animals (80) to TNFα induces insulin resistance, whereas neutralization of TNFα increases insulin sensitivity and reduces hyperglycemia in a type II diabetes animal model (81). Absence of TNFα or TNFα receptors by gene knock-out significantly improves insulin sensitivity in obesity animal models (82).

Mechanisms have been proposed for TNFα induced insulin resistance in adipocytes as well as systemically (83). TNFα inhibits phosphorylation of insulin receptor and insulin receptor substrate-1 (IRS-1) through the inhibitor kB kinase-β (IKK-β). NF-kB activation by TNFα is obligatory for repression of adipocyte-aboundant genes essential for adipocyte function, and is also sufficient to inhibit PPAR-gamma-mediated gene transcription. TNFα also stimulate lipolysis and other cytokine expression in adipose tissue, and triggers FFA release. In fact, plasma FFVs levels increase before overt hyperglycemia in some animal models of insulin resistance (83). There are extensive evidence implicating excess plasma FFA in induction and progression of systemic insulin resistance. In hepatocytes, FFAs contribute to excessive glucose and VLDL production. In muscle cells, high level of FFA impair insulin signaling and promote FFA oxidation leading to greatly decreased glucose ox Currently available insulin sensitizing drugs, which belong to PPAR-gamma agonist, inhibit TNFα-induced adipocytes gene expression profile through NF-kB pathway (84). As adipocyte-derived TNFα functions as autocrine or paracrine factor, systemic delivery of TNFα antibody may not be effective in blocking the biological activity of locally expressed TNFα in adipose tissue (85). NATURA, which represents a new type of small molecule TNFα inhibitor distributing through simple diffusion, could therefore be effective agent to block the function of locally expressed TNFα and potentially useful in the treatment of type 2 diabetes.

Type I diabetes mellitus is an autoimmune disease characterized by mononuclear cell infiltration in the islets of Langerhans and selective destruction of the insulin producing beta cells. While CD8+ T cells may be important initiators, CD4+ T cells (86) and macrophages (87, 88), are the major cellular effectors of the immune process leading to beta cell death. Activated macrophages directly secrete IL-1beta, IL-6, IL-12, TNFalpha, indirectly trigger INF-gamma production from activated T cells. The involvement of cytokines like TNFalpha, INF-gamma, IL-1beta, IL-6 and IL-10, in the pathogenesis of type 1 diabetes has been well clarified through correlation studies of cytokine expression and development of type 1 diabetes, cytokine augmentation studies and cytokine deficiency studies (89). In addition to cytokine neutralizing antibodies and soluble cytokine receptors, anti-inflammatory compounds also show the effects of delaying or preventing the onset of type 1 diabetes in animal models.

Diabetes pathogenesis, from insulitis to complete destruction of the beta cells, is a relatively chronic process. Meisoindigo, NATURA and other derivatives inhibit pro-inflammatory cytokines and stimulates ant-inflammatory cytokines and so can be used as agents to prevent or delay the onset of the disease, as well as to treat them.

In summary, dysregulation of cytokines is involved in a variety of diseases, including inflammatory-related diseases and those normally not considered inflammatory-related diseases. A molecule that is capable of modulating both pro- and anti-inflammatory cytokines should provide therapeutic benefits with minimal side effects for all types of diseases related to dysfunction of these inflammation components. As demonstrated in the present invention, the nature of Meisoindigo, a representative small molecule of derivatives of isoindigo, indigo and indirubin, on the regulation of expression/secretion of multiple pro/anti-inflammatory cytokines, allows this class of compounds to be effectively used to treat of various inflammatory-related disorders associated with pro-inflammatory cytokine expression.

EXAMPLES

Example 1

Meisoindigo Reduces the Secretion of IL-β in Human Monocytic Cell Line THP-1 Cells Materials and Methods Materials: Meisoindigo and NATURA were synthesized by Natrogen Therapeutics, Inc, purified by high performance liquid chromatography (HPLC) with a purity of 98.5%, and their structures confirmed by mass spectrometry and nuclear magnetic resonance (NMR). Meisoindigo is a dark-reddish crystal, with a molecular weight of 376. It was prepared in a solution of dimethyl sulfoxide (DMSO), and stored under −20° C. for the experiments in vitro. Human monocytic cell line, THP-1 (90), was purchased from ATCC. The cells were maintained according to the supplier's instructions. Approximately $1 \times 10^5$ cells/ml were cultured at 37° C., 5% $CO_2$ for 24 hours in Modified RPMI-1640 Medium (Invitrogen) supplemented with 10% FBS.

Figure 2:
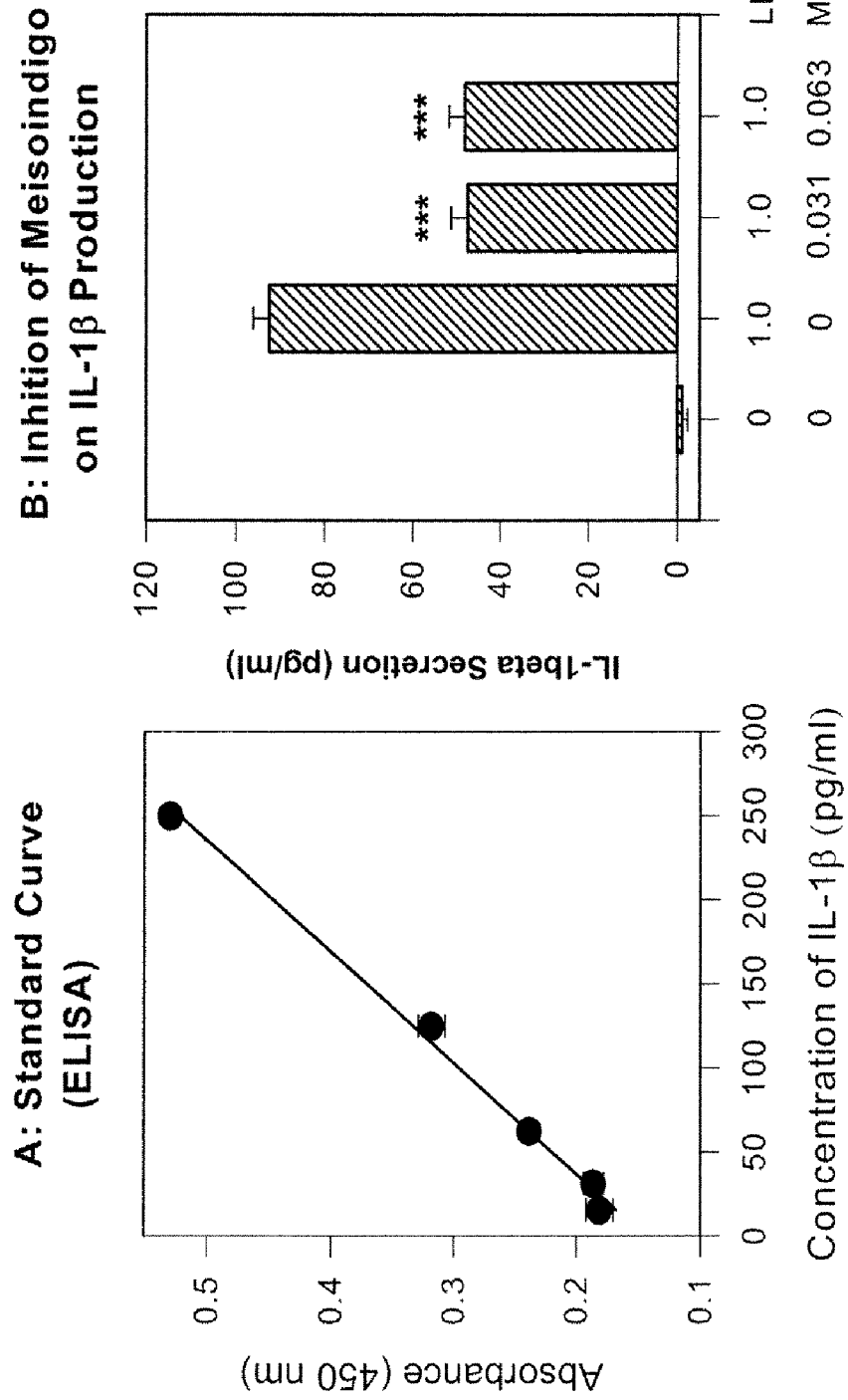
FIG. 2 shows the effect of Meisoindigo on the secretion of IL-1β in LPS stimulated human monocytic THP-1 cells. Inhibitory effect of Meisoindigo on IL-1β production in LPS-stimulated human monocytic THP-1 cells. The THP-1 cells were treated/stimulated with and without 1 μg of lipopolysaccharide (LPS, Sigma), and exposed for 24 hrs to a series of concentrations of Meisoindigo (from 31.25 nM to 16,000 nM). Viability of cells was examined under the microscope after trypan blue staining. Protein levels of IL-1β secreted into the culture media were measured by ELISA and calculated from its standard curve (panel A) using an assay Kit from R&D Systems as described in Materials and Methods in Example 1 below. The student t-test was used to determine the statistically significance, *** indicates P<0.001. As shown in panel B, Meisoindigo significantly inhibits IL-1β production at concentration as low as 31 nM.

Methods: The cells were stimulated with or without 1 μM of lipopolysaccharide (LPS, Sigma), and exposed for 24 hours to different concentrations of Meisoindigo (from 31.25 nM to 16,000 nM). Viability of cells was examined under microscope after trypan blue staining. Protein levels of IL-1β secreted into the culture media by the cells were then measured by ELISA and calculated from its standard curve using an assay Kit from R&D Systems according to instructions provided by the supplier. The method was established and validated by a good standard curve obtained. An example of the standard curve is shown in FIG. 2, panel A.

Statistical Analysis: All data were expressed as a mean±SD. Statistical significance of any difference between the control (LPS) and experimental groups was determined by the Student's t-test. P values between the 2 groups must be at least smaller than 0.05 to be considered statistically significant.

Results and Discussion

IL-1β is a pleiotropic pro-inflammatory cytokine involved in the pathological process of various inflammatory-related diseases. To elucidate the activity of Meisoindigo, a representational small molecule of derivatives of indigo, isoindigo and indirubin, against inflammation, we examined the activity of Meisoindigo on the secretion of IL-1β in human monocytic THP-1 cells. As shown in FIG. 2, panel B, the basal level of IL-1β in human monocytic THP-1 cells was found to be undetectable. It has been demonstrated previously that increases of protein IL-1β and mRNA levels in response to lipopolysaccharide (LPS), predominantly are a result of increased transcription of the gene (91, 92). In this invention, we also observed that upon stimulation of LPS, the THP-1 cells secreted a large amount of IL-1β into the medium (92.38±3.667 pg/ml, FIG. 2, panel B). Interestingly, the stimulated secretion of IL-β was significantly inhibited by simultaneously exposing the cells to Meisoindigo. Most importantly, we found that Meisoindigo was a potent, but also moderate IL-1β inhibitor.

This characteristic will be an advantage to patients for high efficacy with lesser side effects when it is used for the treatment of inflammatory disorders. Potent, because over 50% reduction of the LPS mediated IL-1β secretion was repeatedly achieved when the cells were exposed to Meisoindigo at concentrations as low as 31.25 nM; moderate, because increasing the concentration of Meisoindigo up to 8 µM did not result in further reduction of the secretion, indicating that the activity reached was maximal. This is different from the effect of Meisoindigo or NATURA on the inhibition of cyclin-dependent kinases (CDKs) in which a much higher concentration is needed for the 50% inhibition of CDK activity (approximately 1.6 µM) in LNCaP prostate cancer cells as demonstrated in our previous patent.

The last point is significant since the prior art EP 1 079 826 only set out to inhibit CDKs, rather than cytokines. As a result, much lower concentrations of medicaments are employed in the present invention as compared to the prior art. Furthermore, particular derivatives may also be more suitable for cytokine inhibition as compared to CDK inhibition.

Example 2

Figure 3:
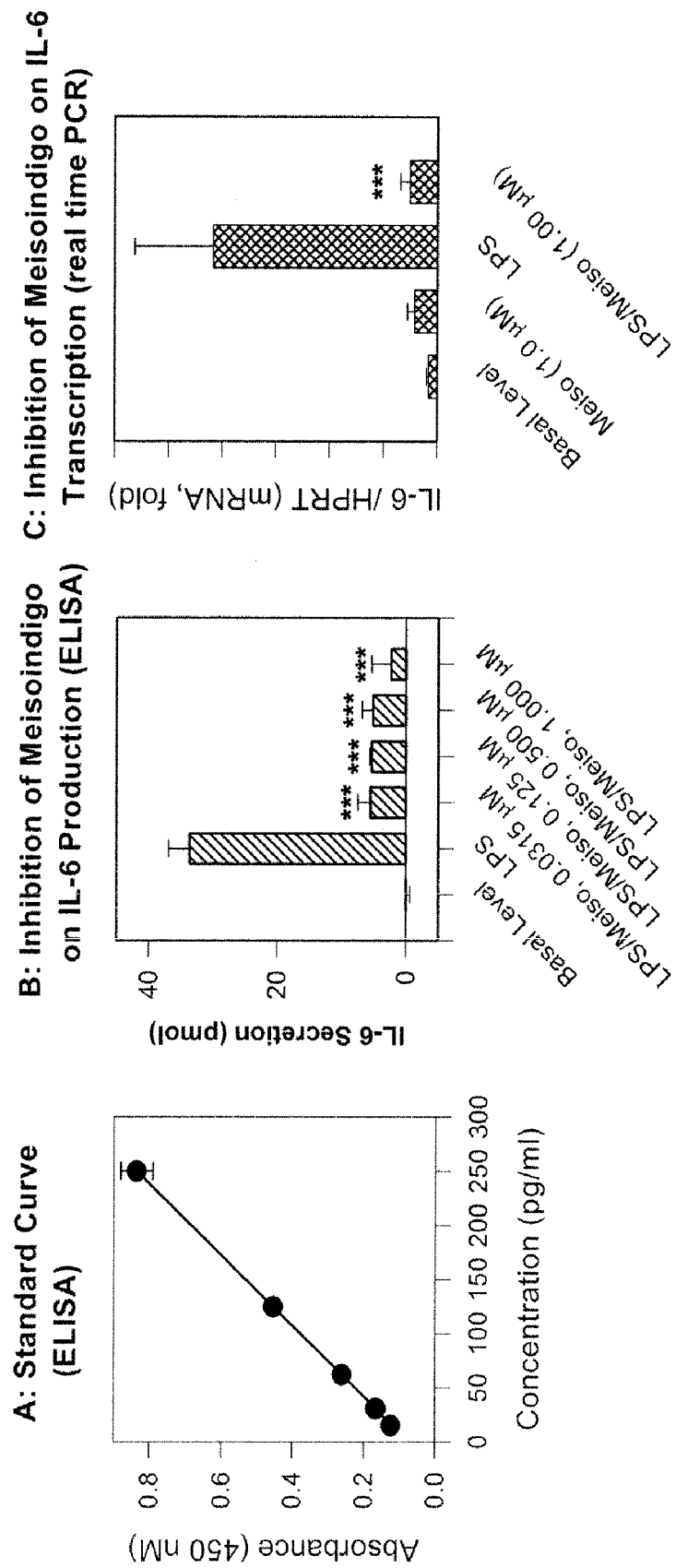
FIG. 3 shows the effect of Meisoindigo on the secretion and expression of IL-6 in LPS stimulated human monocytic THP-1 cells. Effects of Meisoindigo on the production (panel B) and transcription (panel C) of IL-6 in LPS-stimulated THP-1 cells: THP-1 cells were treated/stimulated with and without 1.0 μg/ml of LPS and exposed to a series of concentrations of Meisoindigo (from 0.031 to 16 μM) for 24 hrs. The IL-6 protein in the media was measured by ELISA, and the IL-6 transcription in cells were measured by real time PCR as described in Materials and Methods in Example 2 below. Panel A: Standard curve established using the pure IL-6 protein and used for the calculation of the protein production in panel B; Panel C: real time PCR assay for the transcription of IL-6. ***: P<0.001. As shown in panel B and C, Meisoindigo significantly inhibits both secretion and transcription of IL-6.

Meisoindigo Inhibits the Secretion and Expression of IL-6 in Human Monocytic Cell Line THP-1 Cells Materials and Methods Materials: The representative derivative Meisoindigo was used. The cell line and the procedure of ELISA were the same as described in Example 1. Standard IL-6 protein was used to establish a standard curve for the calculation of IL-6 in the medium secreted by the cells (LPS-stimulated or non-stimulated cells in the presence or absence of Meisoindigo). A typical standard curve is shown in FIG. 3, panel A. Statistical analysis also followed the method described in Example 1.

Methods:

Real Time PCR: The effect of Meisoindigo on the transcription of IL-6 (RNA levels) was determined by a technique of real time polymerase chain reaction (real time PCR). Total RNA was extracted using a Qiagen Rneasy minit kit, and the HPRT gene was used as internal control.

Human monocytic THP-1 cells at exponential growth phase were exposed to 1 µg/ml of LPS, 1 µM of Meisoindigo, or 1 µg/ml of LPS plus 1 µM of Meisoindigo for 24 hours. The cells were then harvested, washed and total RNA extracted for real time PCR assay. Total RNA (300 ng) was treated with DNase I (Promega, Madison, Wis.), and SuperScript II (Invitrogen, Carlsbad, Calif.) and oligo(dT) were used for reverse transcription according to the manufacturers' instructions. Real-time PCR reactions were performed in a 25-µL volume containing diluted cDNA, Sybr Green PCR Master Mix (Applied Biosystems), and 2.5 µM each IL-6 gene-specific primer: R: 5'-TCAATTCGTTCTGAAGAGG (SEQ ID NO. 1) and F: 5'-CCCCCAGGAGAAGATTCC (SEQ ID NO. 2). An ABI SDS7700 analyzer (Applied Biosystems) was used at 50° C. for 2 minutes and 95° C. for 10 minutes, followed by 40 cycles at 95° C. for 15 seconds and 60° C. for 1 minute. Test cDNA results were normalized to HPRT internal control measured on the same plate. After cycling, the specificity of amplification was validated by the generation of a melting curve through slow denaturation of the PCR products and then by gel electrophoresis.

Results and Discussion

IL-6 is another key pro-inflammatory cytokine involved in inflammation. Therefore, the effect of Meisoindigo on the secretion/expression was examined. Similar to IL-1β, the basal level of IL-6 was undetectable in human monocytic THP-1 Cells. Upon stimulation with 1 µg/ml LPS, the cells moderately secreted IL-6 into the media (33.64±3.29 pg/ml). Meisoindigo was found to strongly inhibit the secretion of IL-6 in the LPS stimulated THP-1 cells. Approximately 85% of the reduction of secretion was observed when the stimulated cells were exposed to Meisoindigo at the lowest concentration of 31.25 nM of the experiment (P<0.001) (FIG. 3, panel B).

To explore whether the reduction of IL-6 secretion mediated by Meisoindigo was due to its inhibition on the LPS stimulated expression of IL-6, a real time PCR was applied to measure the effect of Meisoindigo on the IL-6 mRNA transcription. As shown in FIG. 3, panel C, a significant induction of IL-6 transcription was observed when the THP-1 cells were exposed to 1 µg/ml LPS, which is consistent with the previous reports (93). Interestingly, the LPS-induced IL-6 transcription could be completely suppressed by exposing the LPS-stimulated THP-1 cells to 1 µM of Meisoindigo (P<0.001). This finding thus indicates that the inhibition of Meisoindigo on LPS-stimulated secretion of IL-6 probably results from the suppression of the agent on LPS-mediated IL-6 production in THP-1 cells.

Stimulation of LPS on human monocytes activates IL-6 transcriptional signaling pathways. LPS can bind to a protein termed a LPS binding protein (LBP). It has been shown that after its transfer by LBP to the CD14 receptor, LPS interacted with the signaling receptor TLR4 and the accessory protein MD-2. This interaction resulted in the activation of NF-κB and 3 MAP kinases, thus increasing IL-6 transcription (94, 95). Whether suppression of Meisoindigo on LPS-mediated IL-6 transcription is due to the interruption of the signal transduction pathways needs to be further investigated.

Example 3

Meisoindigo Suppresses the Secretion of TNF-α in Human Monocytic THP-1 Cells

Materials and Methods

Figure 4:
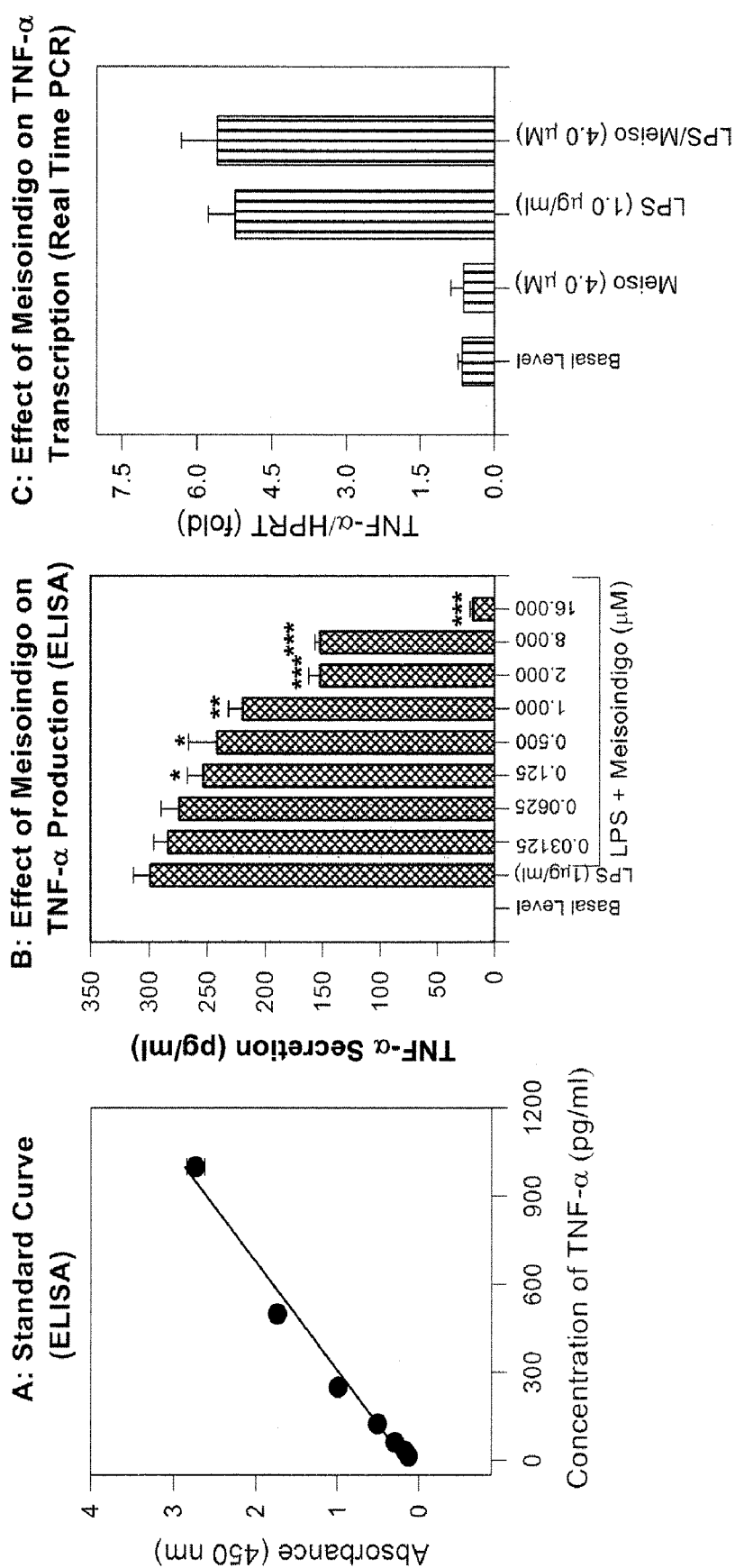
FIG. 4 shows the effect of Meisoindigo on TNF-α secretion and expression in human monocytic THP-1 cells. Effects of Meisoindigo on the protein production (panel B) and gene transcription (panel C) of TNF-α in LPS-stimulated THP-1 cells: THP-1 cells were treated/stimulated with and without 1.0 μg/ml of LPS and exposed to a series of concentrations of Meisoindigo (from 0.031 to 16 μM) for 24 hrs. The TNF-α protein in the media was measured by ELISA, and its transcription in cells was measured by real time PCR technology as described in Materials and Methods in Example 3 below. Panel A: Standard curve established using the pure TNF-α protein and used for the calculation of the protein production in panel B. A concentration-dependent inhibition of Meisoindigo on TNF-α secretion was obtained (panel B). Panel C: real time PCR assay for the transcription of TNF-α. No effect of the agent on TNF-α transcription was observed. ***: P <0.001.

The representative derivative Meisoindigo was used. The cell line and the procedure of ELISA to measure secretion of TNF-α were the same as described in Example 1, except the standard TNF-α protein was used to establish a standard curve for the calculation of the protein secreted in the medium by the cells (LPS-stimulated or non-stimulated cells in the presence or absence of Meisoindigo). A typical standard curve is shown in FIG. 4, panel A.

The effect of Meisoindigo on the transcription of TNF-α (RNA levels) was determined by a technique of real time PCR using the same procedures described in Example 2, except the specific primers for TNF-α were used as follows: 5'-TGC-CCAG-ACTCGGCAAAG (SEQ ID NO. 3), and 5'GGAGAAGGGTGACCGACT (SEQ ID NO. 4). Total RNA was extracted using a Qiagen Rneasy minit kit, and the HPRT gene was used as internal control.

Human monocytic THP-1 cells grown exponentially were exposed to 0.1 µg/ml of LPS, 4 µM of Meisoindigo, or 1 µg/ml of LPS plus 4 µM of Meisoindigo for 24 hours. The cells were then harvested, washed and total RNA extracted for real time PCR assay as described in Example 2.

Results and Discussion

TNF-α is a crucial pro-inflammatory cytokine investigated extensively during the past decade due to its important biological functions against cancer and its pathological role in the inflammatory disorders. Several inhibitors of TNF-α have been marketed for the treatment of various inflammatory-related diseases. As a potential anti-inflammatory agent, we explored a role of Meisoindigo in the regulation of TNF-α in this invention.

As an established model system, stimulation of THP-1 cells with LPS resulted in a huge secretion of TNF-α (FIG. 4, panel B). However, Meisoindigo effectively inhibited the secretion of TNF-α in the LPS-stimulated THP-1 cells in a concentration-dependent manner (FIG. 4, panel B). Approximately 50% reduction of the secretion was achieved when stimulated cells were exposed to 2.0 µM of Meisoindigo for 24 hours (P<0.001, as compared LPS plus Meisoindigo with LPS alone) at which no apoptotic cells were observed using trypan blue staining. Increasing the concentration of Meisoindigo up to 8 µM did not cause further reduction of TNF-α secretion while no cell deaths were observed. A complete inhibition was obtained however when the stimulated cells were treated with 16 µM of Meisoindigo at which approximately only 20% apoptotic cells appeared.

Real time PCR assays showed no effect of Meisoindigo (4 µM) on TNF-α mRNA levels (FIG. 4, panel C), indicating that reduction of TNF-α production in LPS-stimulated THP-1 cells by Meisoindigo occurs at post-transcriptional level. It is well established that AU-rich elements (ARE) in the TNF-α mRNA 3' UTR are involved in mRNA stability and translational efficiency (96). TNF-α ARE is a target of the mRNA-stabilizing factor HuR (97). Maturation of TNF-α mRNA is affected by a cis-element (2-APRE) in the 3'UTR, which renders splicing of TNF-α precursor transcripts dependent on activation of RNA-activated protein kinase (PKR) (98).

Although the mechanisms by which Meisoindigo inhibits the secretion of TNF-α in LPS-stimulated THP-1 cells need to be established, Meisoindigo is a novel small molecule inhibiting TNF-α without cytotoxicities, which would make it an ideal medicine for the treatment of various inflammatory-related diseases.

Example 4

Meisoindigo Stimulates the Secretion of IL-10 in Human Monocytic THP-1 Cells

Materials and Methods

Meisoindigo and the THP-1 cell line used in this Example were the same as described in Example 1. The procedures of ELISA to measure the secretion of IL-10 also followed the procedures described in Example 1, except the standard IL-10 protein was used to establish the standard curve (FIG. 5, panel A) for the calculation of the protein secreted in the medium by the cells (LPS-stimulated or non-stimulated cells in the presence or absence of Meisoindigo).

Results and Discussion

Figure 5:
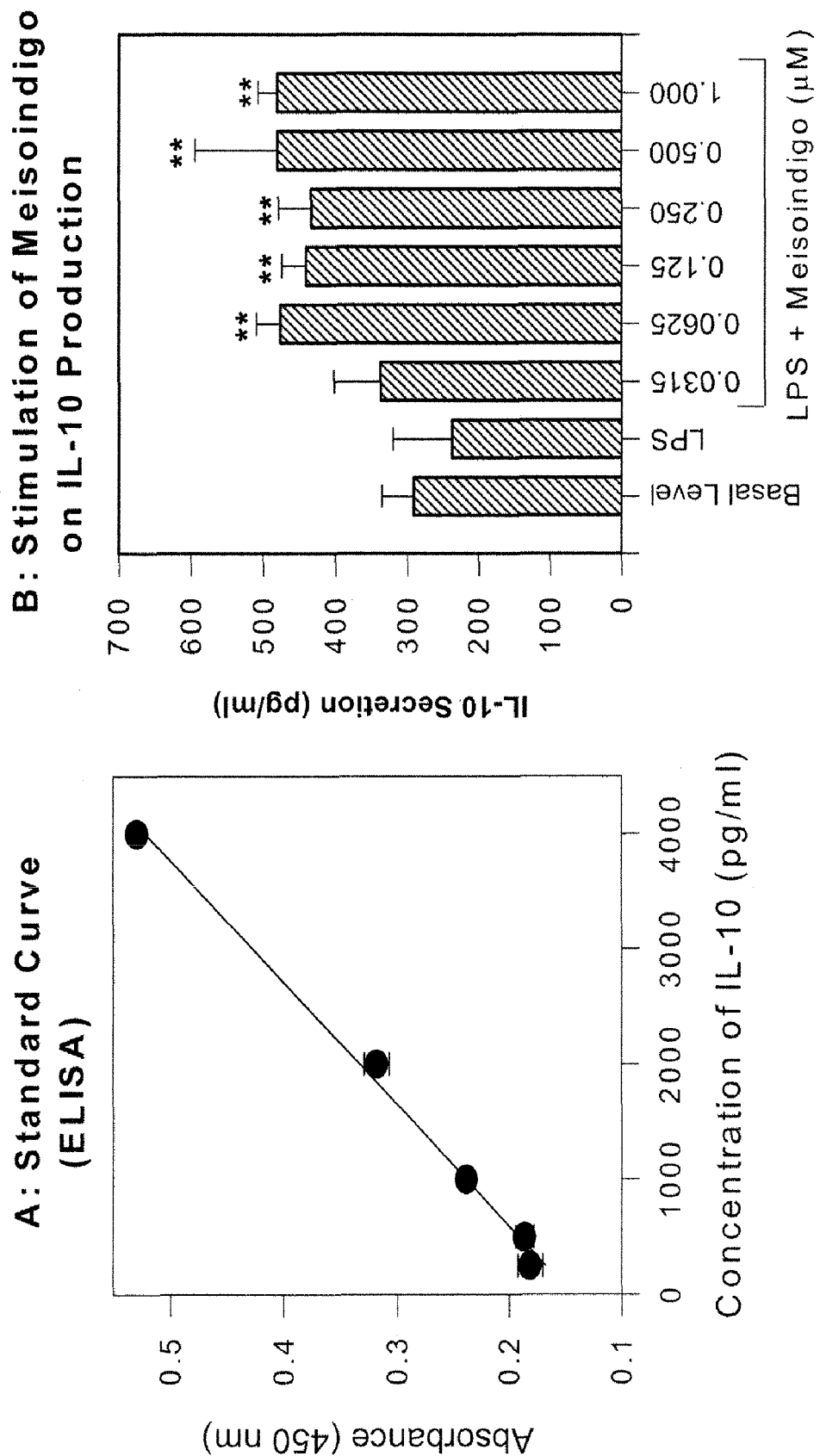
FIG. 5 shows stimulation of IL-10 by Meisoindigo in THP-1 cells. Stimulation of Meisoindigo on the production of IL-10 in LPS-treated THP-1 cells: THP-1 cells were treated with and without 1.0 μg/ml of LPS and exposed to a series of concentrations of Meisoindigo (from 0.031 to 16 μM) for 24 hrs. The IL-10 protein in the media was measured by ELISA as described in Materials and Methods in Example 4 below. Panel A: Standard curve established using the pure IL-10 protein and was used for the calculation of the protein production in panel B. While inflammatory stimulant LPS decreased the protein level of IL-10, Meisoindigo significantly increased the protein production, and the maximal stimulation effect occurred at 62.5 nM with approximately 2-fold increase of IL-10 secretion (panel B). ***: P<0.01.

The functioning of the immune system is finely tuned by the activities of pro-inflammatory and regulatory mediators or cytokines, and inflammatory-related diseases have been considered a result of imbalance between these types of molecules (41, 46). To understand whether the anti-inflammatory effects of small molecules claimed in this invention are capable of induction of regulatory cytokines, the effect of Meisoindigo on the secretion of IL-10 was investigated. As shown in FIG. 5, panel B, a moderate but significant stimulation of IL-10 secretion in THP-1 cells was observed. Approximately 60% increase in the IL-10 secretion was achieved when the THP-1 cells were treated with 0.0625 µM of Meisoindigo (P<0.05). In contrast, as an inflammatory stimulator, LPS slightly decreased the secretion of cytokine.

Example 5

Meisoindigo and Its Derivatives, at Low Concentrations, Select Cytokines, Rather than CDKs as Primary Molecular Targets Materials and Methods Materials: Meisoindigo and NATURA were synthesized by Natrogen Therapeutics, Inc, as described in above examples.

Human monocytic cell line, THP-1 (90), was purchased from ATCC. The cells were maintained according to the supplier's instructions. Approximately $1 \times 10^5$ cells/ml were cultured at 37° C., 5% $CO_2$ for 24 hours in Modified RPMI-1640 Medium (Invitrogen) supplemented with 10% FBS.

Methods:
1) Effects of Meisoindigo and NATURA on the expression/secretion of cytokines IL-1β, IL-6, IL-10: The human monocytic THP-1 cells grown exponentially were stimulated with or without 1 µM of lipopolysaccharide (LPS, Sigma), and exposed for 24 hours to different concentrations of Meisoindigo and NATURA (from 31.25 nM and 62.5 nM), respectively. Viability of cells was examined by trypan blue exception assay. Protein levels of IL-1β secreted into the culture media by the cells were then measured by ELISA and calculated from its standard curve using an assay Kit from R&D Systems according to instructions provided by the supplier as described in the examples of 1 to 4.
2) Effects of Meisoindigo and/or NATURA on activity of cyclin dependent kinases (CDK) in THP-1 cells (99): THP-1 cells grown exponentially were exposed to 31.25, 62.5, and 1500 nM of Meisoindigo or NATURA for 24 hr, respectively. The cells were harvested, washed, and total proteins extracted as described previously (100). One hundred µg of the proteins were immuno-precipitated using antibodies against either cdk2, cdk4/6 or cyclin D1 overnight at 4° C. in the presence of a cocktail of protease inhibitors. The immuno-precipitates were washed 4 times with protein extraction buffer and once with kinase assay buffer, and reacted with 75 µg/ml histone H1 in the presence of [γ-$^{32}$P]-ATP (10 µCi/10 µM). The phosphorylated histone H1 (represent cdk activity) was measured by scintillation counting or by SDS-polyacrylaimde gel electrophoresis (101, 102).
3) Statistical Analysis: All data were expressed as a mean±SD. Statistical significance of any difference between the control (LPS) and experimental groups was determined by the Student's t-test. P values between the 2 groups must be at minimum smaller than 0.05 to be considered statistically significant.

Results and Discussion

Since it has been shown that indirubin and its derivatives inhibited cyclin dependent kinases, it thus could be an effective treatment of diseases associated with the loss of proliferation control via CDK inhibition. To examine which cellular molecules are primary targets related to the anti-inflammatory properties of this class of compounds, we compared how Meisoindigo and NATURA modulated n activities of CDKs and cytokines under the same experimental low concentration conditions.

Figure 6:
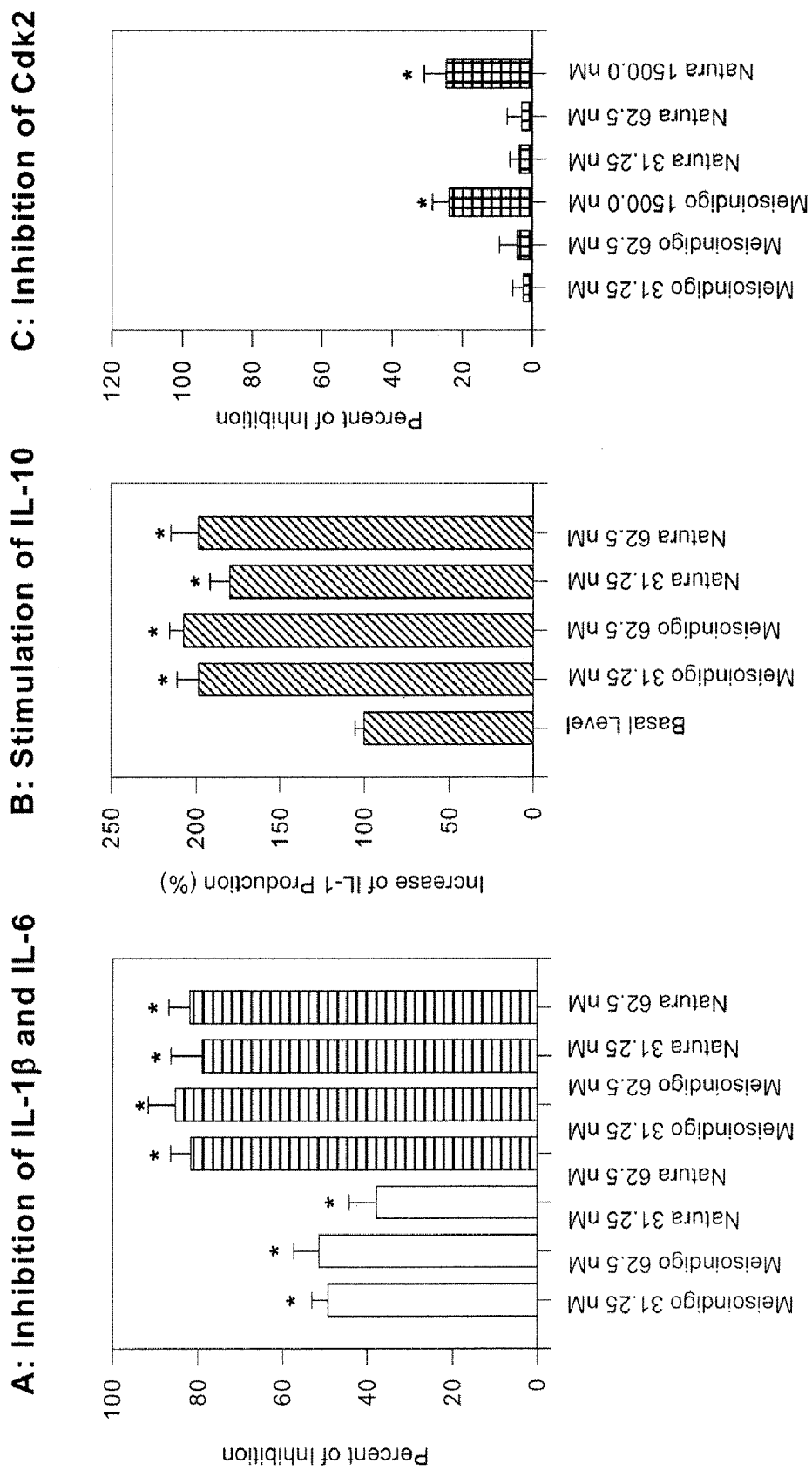
FIG. 6 shows the effects of Meisoindigo and NATURA on the Expression of Pro-inflammatory Cytokines and Cyclin-dependent Kinases in THP-1 cells: The THP-1 cells grown exponentially were stimulated with (panel A and B) and without (panel C) 1 μg LPS, and exposed for 24 hrs to the indicated concentrations of Meisoindigo or NATURA. Viability of cells was examined by trypan blue exception assay. Protein levels of IL-1β, IL-6 and IL-10 secreted into the culture media were measured by ELISA as described in the above examples using an assay Kit from R&D Systems as described in Materials and Methods of Example 5 below. The student t-test was used to determine the statistically significance, * indicates P<0.001. Meisoindigo and NATURA significantly inhibit production of IL-1β and IL-6, and promoted production of IL-10 at concentrations of 31.25 and 62.5 nM. In contrast, no inhibitory effect of the compounds on CDK2 was observed at the low concentrations (31.25 and 62.50 nM) under same experimental conditions.

As shown in FIG. 6, similar to the observation shown in the Examples 1, 2 and 4, LPS-stimulated increases of the production of IL-1β and IL-6 were significantly inhibited by exposure of the cells to both Meisoindigo and NATURA at as low as 31.25 nM, whereas LPS-mediated suppression of IL-10 in the THP-1 cells were elevated almost 2 fold by both Meisoindigo and NATURA under the similar concentrations (FIG. 6A).

In contrast, under the same exposures, both Meisoindigo and NATURA failed to inhibit activities of cyclin dependent 2, 4 and 6, as well as the levels of cyclin D1 (data not shown). A partial inhibition (23%) of those compounds was only achieved when the cells were treated with 1.5 μM (48-fold higher) of either Meisoindigo or NATURA (FIG. 6B).

In addition, the effect of NATURA on glycogen synthase kinase-3β (GSK-3β), was also investigated in the current invention, since CDK inhibitors usually are also inhibitors of GSK-3β. However, no activity was observed when the cells were exposed to NATURA at as high as 50 μM (data not shown).

Thus, the data in this example clearly shows that Meisoindigo and related class of molecules is able to significantly modulate various cytokines (inhibits pro-inflammatory cytokines, and stimulate anti-inflammatory cytokines) at remarkably low concentration; where no any inhibitory effects on CDK activity is achieved. This demonstrates that at low concentrations compared to those needed for CDK inhibition, that Meisoindigo and its derivatives primarily target, cytokines rather than cyclin dependent kinases. This conclusion is supported by the recently observation that Indirubin and its derivatives are not truly biological CDK inhibitors since the inhibition of CDK by those compounds are through physical aggregation rather than biological reaction (103). Moreover our conclusion is also supported by the clinical observations that total dosage of 8696 mg of Meisoindigo is needed to achieved the maximal remission of chronic myeloid leukemia (CML) (104), whereas only 525 mg of the drug are needed to obtain a complete cure of the inflammatory bowel disease.

Summary

THP-1 cells secreted IL-1β, IL-6, IL-8 and TNF-α, but no IL-2, IL-4, IL-10 and IL-12 after 24 hours of the stimulation of LPS while the basal levels of these cytokines were undetectable by ELISA, which is consistent with the previous reports (93, 105). To evaluate the potential clinical applications of a class of small molecules of derivative of isoindigo, indigo, and indirubin (structures shown as Formulas I, II, and III) in the treatment of various inflammatory-related diseases, we examined the regulatory effects of Meisoindigo, as examples on the secretion and expression of pro- and anti-inflammatory cytokines in a human monocytic THP-1 cell model. The data is summarized in Table 2. Meisoindigo significantly inhibited secretions of pro-inflammatory cytokines IL-1β, IL-6, and TNF-α in LPS-stimulated THP-1 cells, and stimulated the secretion of regulatory cytokine IL-10, but no effects were observed on IL-2 simply because the cells were unable to be stimulated to secrete these pro-inflammatory cytokines. The maximal reductions or stimulations of the secretions of these cytokines are summarized in Table 2.

TABLE 2

Modulation of Meisoindigo on the secretion of pro-inflammatory and regulatory cytokines in LPS-stimulated THP-1 cells

| | Percentage of Maximal Response Without Cytotoxicity | | | |
|---|---|---|---|---|
| Treatment | TNF-α (Inhibition) | IL-1β (Inhibition) | IL-6 (Inhibition) | IL-10 (Stimulation) |
| LPS | 100.00 ± 4.85 | 100.00 ± 3.43 | 100.00 ± 9.78 | −18.27 ± 10.15 |
| LPS/Meisoindigo | 49.20 ± 3.37 | 48.76 ± 3.68 | 83.51 ± 5.41 | 201.97 ± 11.2 |

Reduction of IL-6 secretion by Meisoindigo in LPS stimulated THP-1 cells may be a result of the down-regulation of transcription of the cytokine gene by using a real time PCR technique. Real time PCR assay also showed a moderate inhibition of Meisoindigo on IL-15 in the LPS-stimulated THP-1 cells (data not shown). No such down-regulation was observed for TNF-α gene using the same technology. Although mechanisms by which Meisoindigo and molecules of this class regulate pro- and anti-inflammatory cytokines need to be further investigated, our data in the present invention demonstrates that this class of small molecules is capable of modulating important cytokines related to various inflammatory-related diseases.

During the past several years, strategies targeting pro-inflammatory cytokines have been created several protein-based agents for the treatment of various inflammatory disorders, including TNF-α inhibitors etaercept (ENBREL®), infliximan (REMICADE®; Centocor), adalimumab (HUMIRA®; Abbott) and IL-1 receptor antagonist KINERET®. Early stages of clinical application of these agents indicated that these revolutionary therapeutic agents have been an advancement in the treatment of autoimmune diseases such as IBD, RA, and psoriasis. However, the current injectable protein-based therapies have associated risks, including the potential for increased malignancies, infections and increased congestive heart failure (42). Moreover, those strategies also have limitations and are challenged by the sophisticated cytokine network system. Although several types of small molecules have been shown to be a specific pro-inflammatory cytokine inhibitor, such as inhibitors of TNF-α and NF-κB, and have various advantages over the protein-based agents, targeting a single pro-inflammatory cytokine may not be strong enough to interrupt the inflammatory pathological pathways, and this limits their clinical efficacy.

In contrast, besides all the advantages of small molecules in clinical application, such as the fact that they are easy to make and convenient to administer, most importantly the molecules claimed in the invention not only concurrently suppress various pro-inflammatory cytokines, i.e., IL-1β, IL-6, and TNF-α, but also stimulate anti-inflammatory cytokine IL-10. Moreover these molecules have been demonstrated in our previous patent to induce cell differentiation and inhibit cell proliferation at higher concentration. Thus, they provide greater clinical activity. This conclusion has been supported by remarkable outcomes of the efficacy achieved using Meisoindigo for the treatment of a patient with IBD without any side effects. This demonstration is given in Example 7 of this invention.

Example 6

Meisoindigo Suppresses Induced Acute Ulcerative Colitis in Balb/c Mice

Materials and Methods

Materials: Meisoindigo was synthesized, purified and its structure characterized by Natrogen Therapeutics, Inc. as described in the Examples above. A suspension of Meisoindigo was freshly prepared in 0.5% sodium methylcellulose and given orally for the animal tests described below. DSS (Dextran Sulfate Sodium salt, molecular weight: 36,000-44,000) was purchased from ICN Biomedicals. Other chemicals used in the following experiments were purchased from Sigma.

Pathogen-free female Balb/c mice at 12 weeks of age with body weights from 22 to 25 grams were housed 5 per cage, and given, ad libitum, fresh tap water and commercial rodent pellets. Animal rooms were controlled at 24±2° C. with a relative humidity of 60±5% and a 12 hour light/dark cycle (07:00-19:00 hr).

Induction of Acute Ulcerative Colitis DSS-induced colitis in Balb/c Mice: Colitis was induced by DSS in drinking water (MW 36,000-50,000, ICN biochemicals) as described previously (106). Briefly, the mice were randomly divided into 3 groups composed of 10 mice each. In the negative control group (Group 1), mice were given fresh tap water ad libitum and MF pellets, freshly changed twice a week, for 7 days. In the positive control group (DSS group, or Group 2), 5% DSS in tap water was given for 7 days to induce colitis, and the mice were fed with MF pellets. In the DSS-Meisoindigo group (test group or Group 3), mice were given 5% DSS drinking water and given Meisoindigo orally once a day at a dose of 50 mg/kg for 7 consecutive days. Fecal indications of colitis were recorded daily, including body weight and nature of feces (loose and/or bleeding or occult blood). Mice were then sacrificed. Colon tissues were taken, fixed in 10% formalin/PBS, and embedded in paraffin. To minimize physical artifacts, the removed colon was put onto a thick qualitative filter paper without stretching. The colon was then exposed inside out by cutting it longitudinally. The slides were stained with H&E and blindly examined histochemically by 3 technician/pathologists.

Statistical Analysis

All data was expressed as a mean±SD. Statistical significance of any difference between the control and experimental groups was determined by the Student's t-test with a P value of at least <0.05.

Results and Discussion

All animals in the positive control group gradually manifested loose stool, occult blood, and weight loss after drinking 5% DSS in day 4. In several severe cases (7/10), gross blood adhered to the anus in addition to the above-mentioned symptoms. Although the procedures to induce ulcerative colitis in this experiment were very aggressive, and the symptoms that occurred were very acute (manifested within 4 days), occult blood in the Meisoindigo treated group occurred in only 40% (4/10) of the animals. The other symptoms, such as loose stool, were also less severe than that of the control group. No colitis symptoms were observed in animals from the negative control group (normal mice), FIG. 7, panel A.

Figure 7:
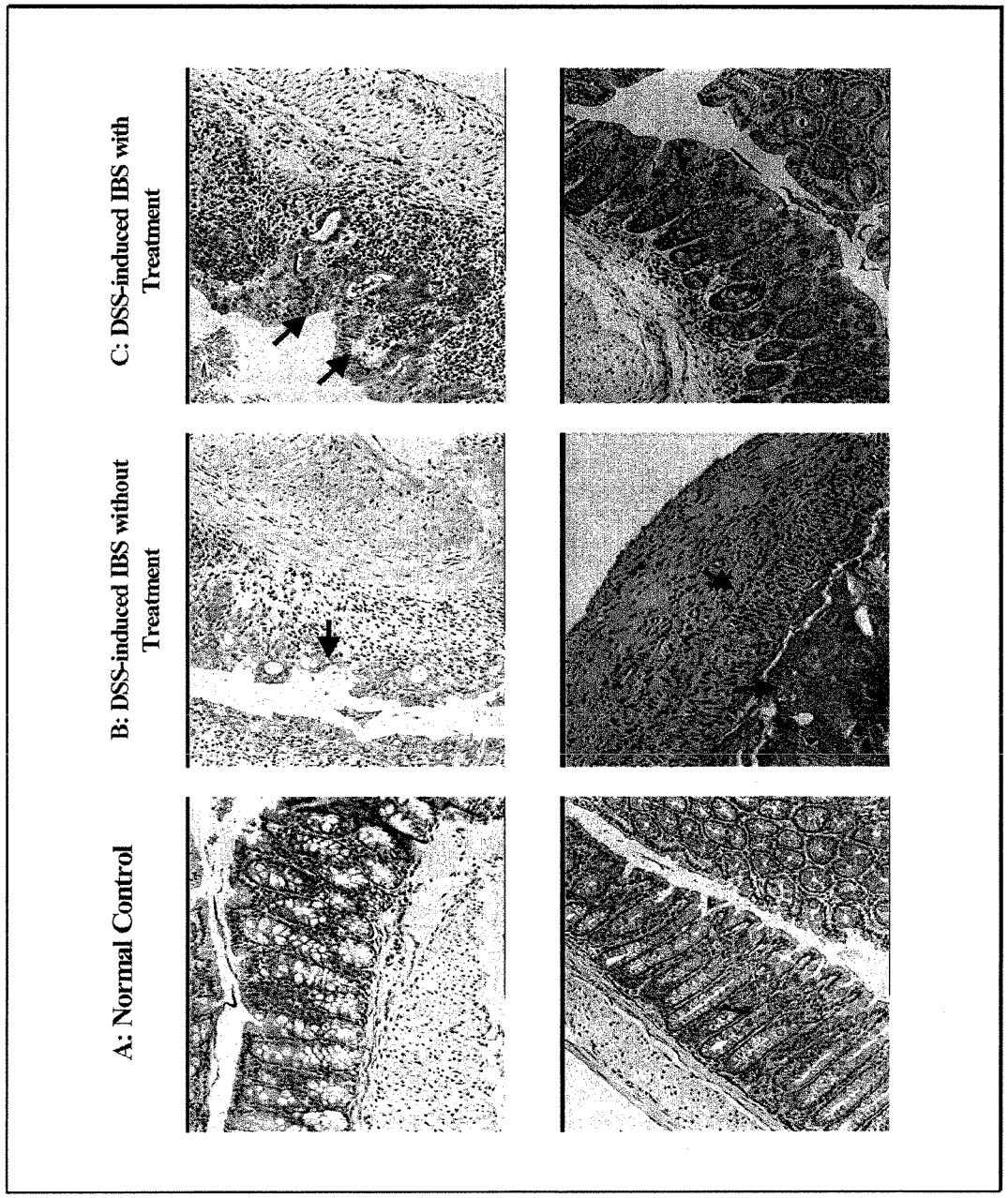
FIG. 7 shows Meisoindigo is effective against DSS-induced acute ulcerative colitis in mice. Examples of histochemistry of colonic walls from 5% DSS-induced acute ulcerative colitis in Balb/c mice treated with and without Meisoindigo (H&E staining, original magnification ×100). The DSS induction and Meisoindigo treatment were performed as described in Materials and Methods in Example 7 below. Panel A shows the normal morphology of the colonic wall from animals in normal control group given drinking water without DSS. Panel B shows the colonic wall from a mouse with acute ulcerative colitis induced by 5% DSS that indicates the presence of severe infiltration of inflammatory cells (lymph follicles, red arrows) and the focal disappearance of mucosal crypts (erosive lesions, blue arrows). Panel C shows the colonic wall from a Meisoindigo treated mouse with acute ulcerative colitis induced by 5% DSS. The morphology is similar to that shown in the normal control (panel A), indicating Meisoindigo is effective against DSS-induced acute ulcerative colitis in mice.

Histological examinations showed that tissues from all animals of the positive control group developed severe ulcerative colitis-like lesions as evidenced by inflammatory cell infiltration, including polymorphonuclear leukocytes and multiple erosive lesions (scores, 1-3). Crypt abscess and regenerated epithelium were also seen in the colonic mucosa (FIG. 7, panel B). To avoid subjective judgment, ulcerative damage of the colon in mice from both positive control and Meisoindigo-treated groups were quantitatively and blindly counted by 3 individual technician/pathologists under microscope. A 55% reduction of the ulcerations in animals of the Meisoindigo-treated group was observed when compared with the positive control group (2.89±1.46 in Meisoindigo-treated group via 6.38±2.20 in the positive control group). FIG. 7, panel C shows the colonic wall from a Meisoindigo treated mouse with acute ulcerative colitis induced by 5% DSS. The morphology is similar to that shown in the normal control (panel A), indicating Meisoindigo is effective against DSS-induced acute ulcerative colitis in mice.

Example 7

Meisoindigo Completely Halted Idiopathic Inflammatory Bowel Disease in a Patient Patient: A 43-year old woman was diagnosed as having over a four-year period, a case of active chronic protocolitis with erosion and features suggestive of idiopathic inflammatory bowel disease. The first diagnosis was performed at North Shore University Hospital Manhasset, Long Island, N.Y. in 1999 by colonoscope. Major symptoms included diarrhea, loose stool and bleeding while her overall condition of health was considered excellent. Clinical-activity index (Table 5) (107) was determined to be between 7 and 8. Her physician prescribed hydrocortisone foam, which she administered for 10 days according to doctor's instructions. However, no therapeutic effect was obtained from this agent. In February 2000, she returned to her home in China and on several occasions, visited Chinese physicians and tried various Chinese herbal medicines suggested, but no therapeutic effect was observed. In early 2002, she went to a well-known and respected Chinese Medical Hospital in Beijing where Flexible Sigmoidoscopy was performed. Again, she was diagnosed as having active inflammatory bowel disease.

TABLE 5

Clinical-Activity Index for the Evaluation of Patients with Ulcerative Colitis (107)

| | | Patient Score | |
| --- | --- | --- | --- |
| Symptom | Standard Score | Before Treatment | After Treatment |
| Diarrhea (No. of daily stools | | | |
| 0-2 | 0 | | |
| 3 or 4 | 1 | | |
| 5 or 6 | 2 | 2 | 0 |
| 7-9 | 3 | | |
| 10 or more | 4 | | |
| Nocturnal diarrhea | | | |
| No | 0 | 0 | 0 |
| Yes | 1 | | |
| Visible blood in stool (% of movements) | | | |
| 0 | 0 | | |
| <50 | 1 | | |

TABLE 5-continued

Clinical-Activity Index for the Evaluation of Patients with Ulcerative Colitis (107)

| Symptom | Standard Score | Patient Score Before Treatment | Patient Score After Treatment |
|---|---|---|---|
| ≧50 | 2 | 2 | 0 |
| 100 | 3 | | |
| Fecal incontinence | | | |
| No | 0 | | |
| Yes | 1 | 1 | 0 |
| Abdominal pain or cramping | | | |
| None | 0 | | |
| Mild | 1 | 1 | 0 |
| Moderate | 2 | | |
| Severe | 3 | | |
| General well-being | | | |
| Perfect | 0 | | |
| Very good | 1 | | |
| Good | 2 | 2 | 0 |
| Average | 3 | | |
| Poor | 4 | | |
| Terrible | 5 | | |
| Abdominal tenderness | | | |
| None | 0 | | |
| Mild and localized | 1 | | |
| Mild to moderate and diffuse | 2 | 0 | 0 |
| Severe or rebound | 3 | | |
| Need for antidiarrhea drugs | | | |
| No | 0 | | |
| Yes | 1 | 1 | 0 |
| Maximal Score | 21 | 9 | 0 |

Figure 8:
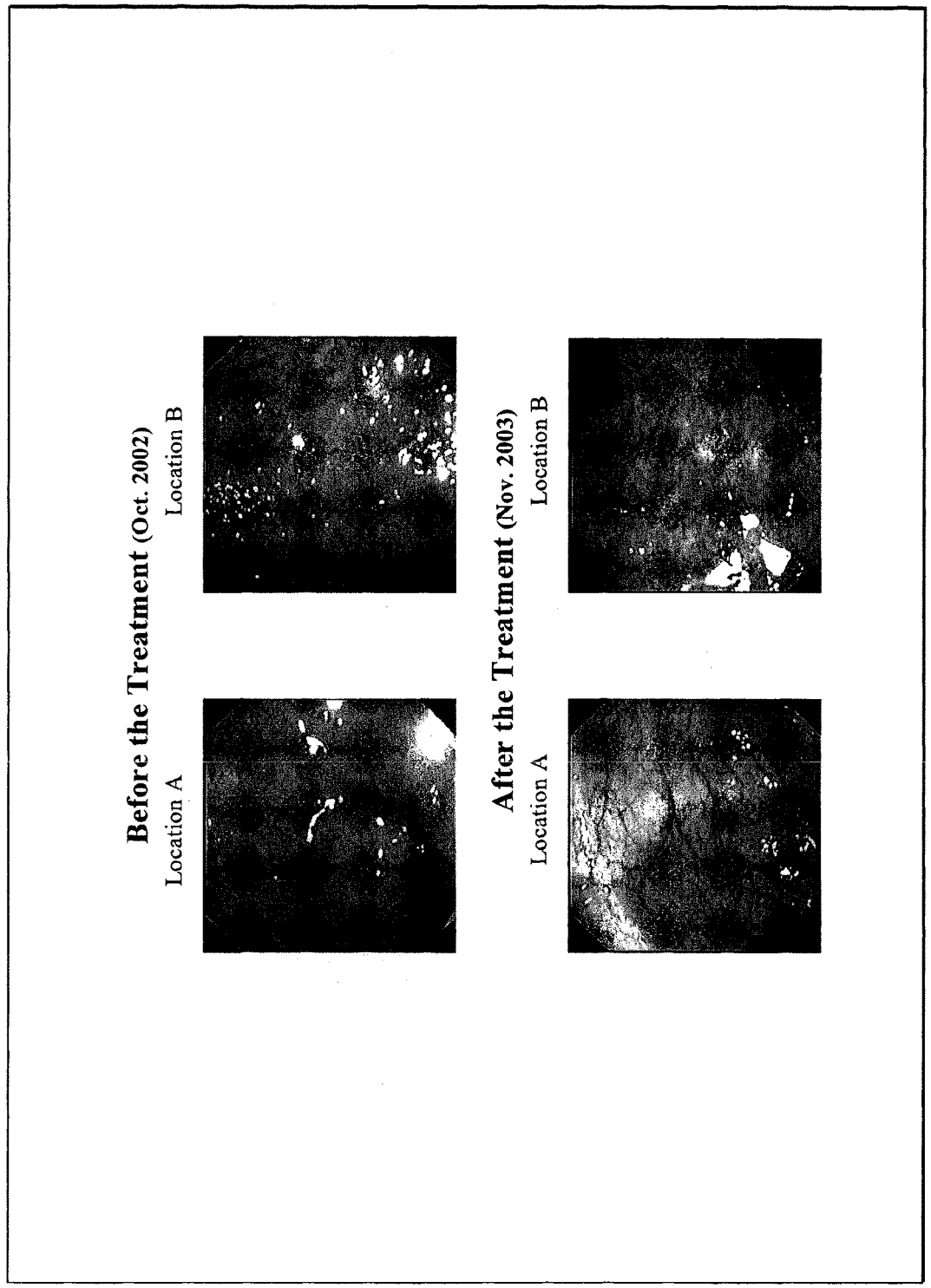
FIG. 8 is photographs of flexible sigmoidoscopy from a patient with inflammatory bowel disease before and after the treatment with Meisoindigo. Upper panels are the photos from two sites of the inflammation (A and B) that clearly show inflammation with severe edema. The pathological examination performed by a pathologist from the Mount Sinai Medical Center in New York City concluded "severely active chronic protocolitis with erosion and features suggestive of idiopathic inflammatory bowel disease". The lower panels are the photos of flexible sigmoidoscopy of the same locations 9 weeks after the patient treated with Meisoindigo. After treatment, the surface of the colon became normal, edema disappeared, and blood vessels can be clearly seen, although there are scars present in location B (lower panel) during the remission. The pathological report concluded "inactive chronic protocolitis suggestive of idiopathic inflammatory bowel disease."

At this time, as previous treatments had no effect, her physician prescribed-several traditional Chinese medicines. She administered these for several months, yet no improvement of her symptoms resulted. During the period of February 2000 to the summer of 2002, she also tried various other traditional Chinese medicines due to the continued and very troublesome nature of her disease, but nothing was successful. Upon returning to the United States in 2002, she went to the Mount Sinai Medical Center, a nationally recognized American center for the treatment of inflammatory bowel disease. In October 2002, her new physician again performed a colonoscope, together with a histological examination of two biopsy samples (A and B) (FIG. 8, panel A, before the treatment). The examinations concluded that two locations (A and B) of the inflammation were "severely active chronic protocolitis with erosion and features suggestive of idiopathic inflammatory bowel disease." The physician prescribed CANASA® (mesalamine in a suppository form), a drug recently approved by the FDA, and considered the best drug available for her condition.

After administering CANASA® for 7 days, her symptoms seemed to be relieved; however, significant side effects simultaneously occurred. These included skin itch, abdominal cramping, pain and bleeding. She then asked her physician for advice and was instructed to use this medication on an intermittently. However, the side effects continued actually worsened each time the medication was used. She then halted all application of this medication.

Meisoindigo was suggested as a potential treatment based on our findings that several pro-inflammatory cytokines could be suppressed Meisoindigo and that anti-inflammatory cytokines, such as cytokine IL-10, can be stimulated. Because of the very minor side effects were reported at a dose of 150 mg per day of this medicine in China for the treatment of chronic myeloid leukemia, Meisoindigo was suggested.

The patient voluntarily administered Meisoindigo at a recommended dose of 25 mg, once a day for a scheduled three weeks of treatment. After the first three doses, the patient obtained complete remission (three days after the treatment) and all inflammatory symptoms disappeared. This resulted in a zero score using the Clinical Activity Index (Table 5). After nine weeks of remission (three weeks on the medicine, three weeks off of the medicine, and three weeks on the medicine again), the patient again visited her physician and requested a Flexible Sigmoidoscopy to determine if her remission was subjective or objective. The Flexible Sigmoidoscopy was performed on Nov. 4, 2003. After reviewing the results her physician concluded that her inflammation completely arrested. Pathological examinations confirmed this conclusion and stated that the A and B specimens were now "inactive chronic protocolitis suggestive of idiopathic inflammatory bowel disease." FIG. 7 shows the photo before (panel A, October 2002) and after the treatment (panel B, Nov. 4, 2003) from the same inflammatory site in the colon-scope examinations performed by the same physician.

Example 8

Therapeutic Effect of Meisoindigo on Chronic Ulcerative Colitis in Balb/c Mice

Meisoindigo has been shown to be a regulator of multiple cytokines IL-1$\beta$, IL-6, IL-10 and TNF-$\alpha$, which are known to be involved in the pathological processes and maintenance of various inflammatory diseases. Meisoindigo has also been shown to be a cytostatic agent that inhibits fast growing cell proliferation and promotes cell differentiation and maturation.

Our previous experiments demonstrated that Meisoindigo has a healing effect in dextran sulfate sodium (DSS)-induced acute, aggressive, ulcerative colitis in Balb/c mice. These results show that Meisoindigo is an effective agent against various chronic inflammatory diseases, including inflammatory bowel disease (IBD).

For this experiment, a DSS-induced chronic ulcerative colitis model was used to verify the in vivo molecular targets, and to evaluate the activity of Meisoindigo against IBD.

Materials and Methods

Materials: Meisoindigo, was been synthesized, purified and structure-characterized by the Natrogen Therapeutics, Inc. A suspension of Meisoindigo was freshly prepared in 0.5% sodium methylcellulose and stored at 4° C. The drug suspension was orally administered for purposes of the animal tests described below. 5-Aminosalicylicacid (5-ASA) was purchased from Sigma. DSS (Dextran Sulfate Sodium salt, molecular weight: 36,000-44,000) was purchased from ICN Biomedicals. Other chemicals used in following experiments were purchased from Sigma.

Pathgen-free Balb/c mice, 12 weeks old, with body weights ranging from 22 to 25 grams, were housed five per cage and fed, ad libitum, fresh tap water and commercial rodent pellets. Animal rooms were controlled at 24±2° C. with a relative humidity of 60±5% and a 12 hr light/dark cycle (07:00-19:00 hr).

Methods: Induction of Chronic Ulcerative Colitis DSS-induced colitis in Balb/c Mice: Chronic ulcerative colitis was induced by DSS in drinking water (MW 36,000-44,000, ICN biochemicals) as described previously [4]. Briefly, 60 mice were randomly divided into 5 groups, 12 mice in each. Group 1 was used as a negative control (without disease-induction), and given fresh tap water ad libitum, and food pellets freshly changed twice a week, from the initiation to completion of the experiment. Group 2-5 were used to chronically induce the ulcerative colitis and to examine Meisoindigo's activity. Animals in Groups 2-5 were fed normally, as was the negative control group, and were also given drinking water containing 5% DSS (MW 36,000-44,000) for 7 days, followed by distilled water for a subsequent 10 days. The animals were again given drinking water containing 5% DSS for 7 days, followed by distilled water for another 10 days. This procedure was repeated for a total of 3 cycles.

After 3 cycles, chronic ulcerative colitis developed and was stabilized as described. Group 2 (positive control group) were fed with saline, and group 3 were treated with 5-ASA at 50 mg/kg/d by gavage as a positive drug based control. Group 4 and 5 were treated with Meisoindigo at dosages of 25 and 75 mg/kg, once a day for 12 days.

During the period of the experiment, disease activity indexes (DAI), reflected by body weights, stool consistency, and occurrence of occult blood or gross rectal blood, were determined and recorded daily by an independent investigator according to methods described previously [108, 110]. Those clinical parameters are comprehensive functional measures similar to subjective clinical symptoms observed in human ulcerative colitis(UC) and correlate well with the degree of histologic healing measured as crypt scores [108-110]. Mice were then sacrificed. Tissues/organs of the spleen, colon, and as well as others were extracted, examined for appearance, and their weights were recorded. To minimize physical artifacts, the removed colon was put on thick qualitative filter paper without stretching. The colon was exposed inside out by cutting longitudinally. All colon tissues were 10% formalin/PBS fixed, paraffin embedded, and slide sections were made. The slides were stained with H&E for histological examination. The slides were examined blindly by technician/ pathologists and photographed. Severities of ulcerative colitis were graded on a scale from 0-3 and expressed as the pathological index according to the standard scoring system: 0, normal; 1, focal inflammatory cell infiltration including polymorphonuclear leukocytes; 2, inflammatory cell infiltration, gland dropout, and crypt abscess; 3, mucosal ulceration. Numbers of lymphoid follicles ulcerative damages were counted in the medical longitudinal sections of the colon under light microscope.

Statistical Analysis

All data were expressed as mean+SD. Statistical significance of any difference between the control and experimental groups were determined by the Student's t-test with P value at least <0.05.

Results and Discussion

Disease Activity Index (DAI): After drinking 5% DSS for 7 days, all mice initially manifested diarrhea and occult blood in their feces with significant decreases in body weight, while no such symptoms were observed in animals fed with distilled water. However, these signs disappeared (DAI reached the nadir in 8-9 days) after the mice were given distilled water for the next 10 days. However, on subsequent administrations of DSS (3 administration cycles), these clinical symptoms did not recover, but rather deteriorated during the 10-day distilled water consumption period.

After the third DSS-feeding cycle, animals were treated for 12 days by gavage with vehicle, 50 mg/kg/day 5-ASA, 25 or 75 mg/kg/day of Meisoindigo. Twenty-four hours after the last administration, the DAI scores were determined for all five groups. As shown in Table 6 below, after cessation of feeding DSS for 12 days, the DAI decreased 50% in vehicle treated group, which was most likely due to self-healing [111]. However, the extent of the DAI decrease in both 5-ASA and two Meisoindigo treated groups was significantly enhanced up to 70%, which reflects a therapeutic response of the drug treatment. The efficacy of Meisoindigo at both doses was equal to that of 5-ASA.

TABLE 6

Disease Activity Index (weight loss, stool consistency, and bleeding/3)

| Agent | | Prior Treatment Mean ± SD | Post Treatment Mean ± SD | Recovery (%) |
|---|---|---|---|---|
| Saline | Female (n = 5) | 2.40 ± 0.2 | 1.07 ± 1.0 | |
| | Male (n = 6) | 2.40 ± 0.2 | 1.33 ± 1.15 | |
| | Mean (n = 11) | 2.40 ± 0.2 | 1.2 ± 1.2 | 50.6 |
| ASA 50 mg/kg | Female (n = 0) | N/A | N/A | |
| | Male (n = 10) | 3.27 ± 0.3 | 0.86 ± 1.0 | |
| | Mean (n = 10) | 3.27 ± 0.3 | 0.86 ± 1.0 | 73.1 (p = 0.031) |
| Meisoindigo 25 mg/kg | Female (n = 5) | 3.20 ± 0.2 | 0.67 ± 1.15 | |
| | Male (n = 7) | 2.73 ± 0.35 | 0.93 ± 1.0 | |
| | Mean (n = 12) | 3.00 ± 0.1 | 0.80 ± 1.06 | 73.3 (p = 0.023) |
| Meisoindigo 75 mg/kg | Female (n = 6) | 3.11 ± 0.68 | 0.93 ± 1.0 | |
| | Male (n = 6) | 3.27 ± 0.75 | 0.97 ± 1.0 | |
| | Mean (n = 12) | 3.22 ± 0.71 | 0.95 ± 1.0 | 70.3 (p = 0.033) |
| None | Female (n = 6) | 0 | 0 | N/A |
| | Male (n = 6) | 0 | 0 | N/A |
| | Mean (n = 12) | 0 | 0 | N/A |

Hemoccult Scores

Table 7, below, shows the hemoccult scores in all groups of treated or untreated animals. Twelve days after cessation of DSS-feeding, the animals in vehicle treated group showed a slight recovery (27.2%), which was consistent with the chronic nature of colitis induced by 3 consecutive DSS-feeding cycles, as reported previously [4]. In contrast, a significant improvement was observed in both 5-ASA and Meisoindigo treated groups. The animals in the low dose Meisoindigo group showed the best therapeutic response (87%) as compared with 75.7% in the high dose group. The low dose was also better than the positive control 5-ASA with an 80% recovery. The Meisoindigo healing of the bleeding in DSS induced IBD in animals is also consistent with a previous observation that the Meisoindigo treatment produced a speedy termination of bleeding in a patient with ulcerative colitis.

Qualitative Histology

The traverse (mid) sections of colons from mice were prepared in formalin for paraffin embedding. Slides were stained with H&E. Two mice from each group were used for slide preparation, and for examination of the quality of the slide preparation and the staining.

Histology of vehicle treated animals showed loss of surface epithelium, loss of glands, and the presence of chronic inflammation. Slides of animals in both Meisoindigo treated groups are more like the 5-ASA groups that showed less erosion, milder inflammatory infiltrates as compared to that from mice with IBD.

TABLE 7

Score for Occult blood

| Agent | | Prior Treatment Mean + SD | Post Treatment Mean + SD | Recovery (%) |
|---|---|---|---|---|
| Saline | Female (n = 5) | 2.4 + 0.89 | 1.2 + 1.09 | 50 |
| | Male (n = 6) | 2.0 + 0 | 2.0 + 0 | 0 |
| | Mean (n = 11) | 2.2 + 0.6 | 1.6 + 0.8 | 27.2 |
| ASA 50 mg/kg | Female (n = 0) | N/A | N/A | N/A |
| | Male (n = 10) | 3.0 + 1.05 | 0.6 + 0.96 | 80.0 |
| | Mean (n = 10) | 3.0 + 1.05 | 0.6 + 0.96 | 80.0 (p < 0.01) |
| Meisoindigo 25 mg/kg | Female (n = 5) | 2.8 + 1.09 | 0.8 + 1.0 | 71.4 |
| | Male (n = 7) | 3.1 + 1.06 | 0 + 0 | 100 |
| | Mean (n = 12) | 3.0 + 1.04 | 0.4 + 0.77 | 86.7 (p < 0.01) |
| Meisoindigo 75 mg/kg | Female (n = 6) | 3.3 + 1.03 | 0.6 + 1.0 | 81.8 |
| | Male (n = 6) | 3.6 + 0.81 | 1.0 + 1.0 | 72.2 |
| | Mean (n = 12) | 3.5 + 0.9 | 0.83 + 1.0 | 76.3 (p < 0.01) |
| None | Female (n = 6) | 0 | 0 | N/A |
| | Male (n = 6) | 0 | 0 | N/A |
| | Mean (n = 12) | 0 | 0 | N/A |

REFERENCES

1. Bebo, B. F., Jr., Yong, T., Orr, E. L., and Linthicum, D. S. Hypothesis: a possible role for mast cells and their inflammatory mediators in the pathogenesis of autoimmune encephalomyelitis. J Neurosci Res, 45: 340-348, 1996.
2. Mennicken, F., Maki, R., de Souza, E. B., and Quirion, R. Chemokines and chemokine receptors in the CNS: a possible role in neuroinflammation and patterning. Trends Pharmacol Sci, 20: 73-78, 1999.
3. Watanabe, T. and Fan, J. Atherosclerosis and inflammation mononuclear cell recruitment and adhesion molecules with reference to the implication of ICAM-1/LFA-1 pathway in atherogenesis. Int J Cardiol, 66 Suppl 1: S45-53; discussion S55, 1998.
4. Sullivan, G. W., Sarembock, I. J., and Linden, J. The role of inflammation in vascular diseases. J Leukoc Biol, 67: 591-602, 2000.
5. Franceschi, C., Bonafe, M., Valensin, S., Olivieri, F., De Luca, M., Ottaviani, E., and De Benedictis, G. Inflamm-aging. An evolutionary perspective on immunosenescence. Ann N Y Acad Sci, 908: 244-254, 2000.
6. Rogers, J. and Shen, Y. A perspective on inflammation in Alzheimer's disease. Ann N Y Acad Sci, 924: 132-135, 2000.
7. Li, Y. J., Oliveira, S. A., Xu, P., Martin, E. R., Stenger, J. E., Scherzer, C. R., Hauser, M. A., Scott, W. K., Small, G. W., Nance, M. A., Watts, R. L., Hubble, J. P., Koller, W. C., Pahwa, R., Stern, M. B., Hiner, B. C., Jankovic, J., Goetz, C. G., Mastaglia, F., Middleton, L. T., Roses, A. D., Saunders, A. M., Schmechel, D. E., Gullans, S. R., Haines, J. L., Gilbert, J. R., Vance, J. M., and Pericak-Vance, M. A. Glutathione S-Transferase Omega 1 modifies age-at-onset of Alzheimer Disease and Parkinson Disease. Hum Mol Genet, 12: 3259-3267, 2003.
8. Maccarrone, M., Bari, M., Battista, N., and Finazzi-Agro, A. Endocannabinoid degradation, endotoxic shock and inflammation. Curr Drug Targets Inflamm Allergy, 1: 53-63, 2002.
9. Lindsberg, P. J. and Grau, A. J. Inflammation and infections as risk factors for ischemic stroke. Stroke, 34: 2518-2532, 2003.
10. DeGraba, T. J. The role of inflammation in atherosclerosis. Adv Neurol, 92: 29-42, 2003.
11. Ito, H. IL-6 and Crohn's disease. Curr Drug Targets Inflamm Allergy, 2: 125-130, 2003.
12. von der Thusen, J. H., Kuiper, J., van Berkel, T. J., and Biessen, E. A. Interleukins in atherosclerosis: molecular pathways and therapeutic potential. Pharmacol Rev, 55: 133-166, 2003.
13. Schmidt, M. I. and Duncan, B. B. Diabesity: an inflammatory metabolic condition. Clin Chem Lab Med, 41: 1120-1130, 2003.
14. Virdis, A. and Schiffrin, E. L. Vascular inflammation: a role in vascular disease in hypertension? Curr Opin Nephrol Hypertens, 12: 181-187, 2003.
15. Tracy, R. P. Inflammation, the metabolic syndrome and cardiovascular risk. Int J Clin Pract Suppl 10-17, 2003.
16. Haugeberg, G., Orstavik, R. E., and Kvien, T. K. Effects of rheumatoid arthritis on bone. Curr Opin Rheumatol, 15: 469-475, 2003.
17. Tanaka, Y., Okada, Y., and Nakamura, T. Inter- and intra-cellular signaling in secondary osteoporosis. J Bone Miner Metab, 21: 61-66, 2003.
18. Williams, J. D. and Griffiths, C. E. Cytokine blocking agents in dermatology. Clin Exp Dermatol, 27: 585-590, 2002.
19. Rutgeerts, P. A critical assessment of new therapies in inflammatory bowel disease. J Gastroenterol Hepatol, 17 Suppl: S176-185, 2002.
20. Rutgeerts, P., Lemmens, L., Van Assche, G., Noman, M., Borghini-Fuhrer, I., and Goedkoop, R. Treatment of active Crohn's disease with onercept (recombinant human soluble p55 tumour necrosis factor receptor): results of a randomized, open-label, pilot study. Aliment Pharmacol Ther, 17: 185-192, 2003.
21. Weinberg, J. M., Saini, R., and Tutrone, W. D. Biologic therapy for psoriasis--the first wave: infliximab, etanercept, efalizumab, and alefacept. J Drugs Dermatol, 1: 303-310, 2002.

22. Cooper, J. C., Morgan, G., Harding, S., Subramanyam, M., Majeau, G. R., Moulder, K., and Alexander, D. R. Alefacept selectively promotes NK cell-mediated deletion of CD45R0+ human T cells. Eur J Immunol, 33: 666-675, 2003.
23. Cather, J. C. and Menter, A. Modulating T cell responses for the treatment of psoriasis: a focus on efalizumab. Expert Opin Biol Ther, 3: 361-370, 2003.
24. Brown, S. L., Greene, M. H., Gershon, S. K., Edwards, E. T., and Braun, M. M. Tumor necrosis factor antagonist therapy and lymphoma development: twenty-six cases reported to the Food and Drug Administration. Arthritis Rheum, 46: 3151-3158, 2002.
25. Weisman, M. H. What are the risks of biologic therapy in rheumatoid arthritis? An update on safety. J Rheumatol Suppl, 65: 33-38, 2002.
26. Antoni, C. and Braun, J. Side effects of anti-TNF therapy: current knowledge. Clin Exp Rheumatol, 20: S152-157, 2002.
27. Mendonca, C. O. and Burden, A. D. Current concepts in psoriasis and its treatment. Pharmacol Ther, 99: 133-147, 2003.
28. Schon, M. P. Animal models of psoriasis—what can we learn from them? J Invest Dermatol, 112: 405-410, 1999.
29. Bessis, N., Doucet, C., Cottard, V., Douar, A. M., Firat, H., Jorgensen, C., Mezzina, M., and Boissier, M. C. Gene therapy for rheumatoid arthritis. J Gene Med, 4: 581-591, 2002.
30. Hochberg, M. C., Tracy, J. K., Hawkins-Holt, M., and Flores, R. H. Comparison of the efficacy of the tumour necrosis factor alpha blocking agents adalimumab, etanercept, and infliximab when added to methotrexate in patients with active rheumatoid arthritis. Ann Rheum Dis, 62 Suppl 2: ii13-16, 2003.
31. Fassas, A. and Kimiskidis, V. K. Stem cell transplantation for multiple sclerosis: What is the evidence? Blood Rev, 17: 233-240, 2003.
32. Furlan, R., Pluchino, S., and Martino, G. Gene therapy-mediated modulation of immune processes in the central nervous system. Curr Pharm Des, 9: 2002-2008, 2003.
33. Ghezzi, P. and Mennini, T. Tumor necrosis factor and motoneuronal degeneration: an open problem. Neuroimmunomodulation, 9: 178-182, 2001.
34. Andreakos, E. T., Foxwell, B. M., Brennan, F. M., Maini, R. N., and Feldmann, M. Cytokines and anti-cytokine biologicals in autoimmunity: present and future. Cytokine Growth Factor Rev, 13: 299-313, 2002.
35. Najarian, D. J. and Gottlieb, A. B. Connections between psoriasis and Crohn's disease. J Am Acad Dermatol, 48: 805-821; quiz 822-804, 2003.
36. Noguchi, M., Hiwatashi, N., Liu, Z., and Toyota, T. Secretion imbalance between tumour necrosis factor and its inhibitor in inflammatory bowel disease. Gut, 43: 203-209, 1998.
37. Autschbach, F., Braunstein, J., Helmke, B., Zuna, I., Schurmann, G., Niemir, Z. I., Wallich, R., Otto, H. F., and Meuer, S. C. In situ expression of interleukin-10 in noninflamed human gut and in inflammatory bowel disease. Am J Pathol, 153: 121-130, 1998.
38. Schreiber, S., Heinig, T., Thiele, H. G., and Raedler, A. Immunoregulatory role of interleukin 10 in patients with inflammatory bowel disease. Gastroenterology, 108: 1434-1444, 1995.
39. Baugh, J. A. and Bucala, R. Mechanisms for modulating TNF alpha in immune and inflammatory disease. Curr Opin Drug Discov Devel, 4: 635-650, 2001.
40. Gabay, C. IL-1 trap. Regeneron/Novartis. Curr Opin Investig Drugs, 4: 593-597, 2003.
41. Palladino, M. A., Bahjat, F. R., Theodorakis, E. A., and Moldawer, L. L. Anti-TNF-alpha therapies: the next generation. Nat Rev Drug Discov, 2: 736-746, 2003.
42. Girolomoni, G., Pastore, S., Albanesi, C., and Cavani, A. Targeting tumor necrosis factor-alpha as a potential therapy in inflammatory skin diseases. Curr Opin Investig Drugs, 3: 1590-1595, 2002.
43. Elliott, M. J., Maini, R. N., Feldmann, M., Long-Fox, A., Charles, P., Bijl, H., and Woody, J. N. Repeated therapy with monoclonal antibody to tumour necrosis factor alpha (cA2) in patients with rheumatoid arthritis. Lancet, 344: 1125-1127, 1994.
44. Moreland, L. W., Baumgartner, S. W., Schiff, M. H., Tindall, E. A., Fleischmann, R. M., Weaver, A. L., Ettlinger, R. E., Cohen, S., Koopman, W. J., Mohler, K., Widmer, M. B., and Blosch, C. M. Treatment of rheumatoid arthritis with a recombinant human tumor necrosis factor receptor (p75)-Fc fusion protein. N Engl J Med, 337: 141-147, 1997.
45. Campion, G. V., Lebsack, M. E., Lookabaugh, J., Gordon, G., and Catalano, M. Dose-range and dose-frequency study of recombinant human interleukin-1 receptor antagonist in patients with rheumatoid arthritis. The IL-1Ra Arthritis Study Group. Arthritis Rheum, 39: 1092-1101, 1996.
46. Feldmann, M. Pathogenesis of arthritis: recent research progress. Nat Immunol, 2: 771-773, 2001.
47. Ji, X. J., Liu, X. M., Li, K., Chen, R. H., and Wang, L. G. Pharmacological studies of meisoindigo: absorption and mechanism of action. Biomed Environ Sci, 4: 332-337, 1991.
48. Dustin, M. L., Rothlein, R., Bhan, A. K., Dinarello, C. A., and Springer, T. A. Induction by IL 1 and interferon-gamma: tissue distribution, biochemistry, and function of a natural adherence molecule (ICAM-1). J Immunol, 137: 245-254, 1986.
49. Strange, P., Skov, L., and Baadsgaard, 0. Interferon gamma-treated keratinocytes activate T cells in the presence of superantigens: involvement of major histocompatibility complex class II molecules. J Invest Dermatol, 102: 150-154, 1994.
50. Subramanian, N. and Bray, M. A. Interleukin 1 releases histamine from human basophils and mast cells in vitro. J Immunol, 138: 271-275, 1987.
51. Grossman, R. M., Krueger, J., Yourish, D., Granelli-Pipemo, A., Murphy, D. P., May, L. T., Kupper, T. S., Sehgal, P. B., and Gottlieb, A. B. Interleukin 6 is expressed in high levels in psoriatic skin and stimulates proliferation of cultured human keratinocytes. Proc Natl Acad Sci USA, 86: 6367-6371, 1989.
52. Schreiber, A. B., Winkler, M. E., and Derynck, R. Transforming growth factor-alpha: a more potent angiogenic mediator than epidermal growth factor. Science, 232: 1250-1253, 1986.
53. Detmar, M., Brown, L. F., Claffey, K. P., Yeo, K. T., Kocher, O., Jackman, R. W., Berse, B., and Dvorak, H. F. Overexpression of vascular permeability factor/vascular endothelial growth factor and its receptors in psoriasis. J Exp Med, 180: 1141-1146, 1994.
54. Dayer, J. M. The pivotal role of interleukin-1 in the clinical manifestations of rheumatoid arthritis. Rheumatology (Oxford), 42 Suppl 2: ii3-10, 2003.
55. Bresnihan, B., Alvaro-Gracia, J. M., Cobby, M., Doherty, M., Domljan, Z., Emery, P., Nuki, G., Pavelka, K., Rau, R., Rozman, B., Watt, I., Williams, B., Aitchison, R., McCabe, D., and Musikic, P. Treatment of rheumatoid arthritis with recombinant human interleukin-1 receptor antagonist. Arthritis Rheum, 41: 2196-2204, 1998.
56. Ishihara, K. and Hirano, T. IL-6 in autoimmune disease and chronic inflammatory proliferative disease. Cytokine Growth Factor Rev, 13: 357-368, 2002.
57. Whalen, J. D., Lechman, E. L., Carlos, C. A., Weiss, K., Kovesdi, I., Glorioso, J. C., Robbins, P. D., and Evans, C. H. Adenoviral transfer of the viral IL-10 gene periarticularly to mouse paws suppresses development of collagen-induced arthritis in both injected and uninjected paws. J Immunol, 162: 3625-3632, 1999.
58. Lechman, E. R., Jaffurs, D., Ghivizzani, S. C., Gambotto, A., Kovesdi, I., Mi, Z., Evans, C. H., and Robbins, P. D. Direct adenoviral gene transfer of viral IL-10 to rabbit knees with experimental arthritis ameliorates disease in both injected and contralateral control knees. J Immunol, 163: 2202-2208, 1999.
59. Glabinski, A. R., Bielecki, B., and Ransohoff, R. M. Chemokine upregulation follows cytokine expression in chronic relapsing experimental autoimmune encephalomyelitis. Scand J Immunol, 58: 81-88, 2003.
60. Diab, A., Zhu, J., Xiao, B. G., Mustafa, M., and Link, H. High IL-6 and low IL-10 in the central nervous system are associated with protracted relapsing EAE in DA rats. J Neuropathol Exp Neurol, 56: 641-650, 1997.
61. Samoilova, E. B., Horton, J. L., Hilliard, B., Liu, T. S., and Chen, Y. IL-6-deficient mice are resistant to experimental autoimmune encephalomyelitis: roles of IL-6 in the activation and differentiation of autoreactive T cells. J Immunol, 161: 6480-6486, 1998.
62. Robertson, J., Beaulieu, J. M., Doroudchi, M. M., Durham, H. D., Julien, J. P., and Mushynski, W. E. Apoptotic death of neurons exhibiting peripherin aggregates is mediated by the proinflammatory cytokine tumor necrosis factor-alpha. J Cell Biol, 155: 217-226, 2001.
63. de Jong, B. A., Huizinga, T. W., Bollen, E. L., Uitdehaag, B. M., Bosma, G. P., van Buchem, M. A., Remarque, E. J., Burgmans, A. C., Kalkers, N. F., Polman, C. H., and Westendorp, R. G. Production of IL-1beta and IL-1Ra as risk factors for susceptibility and progression of relapse-onset multiple sclerosis. J Neuroimmunol, 126: 172-179, 2002.
64. McGeer, E. G. and McGeer, P. L. Inflammatory processes in Alzheimer's disease. Prog Neuropsychopharmacol Biol Psychiatry, 27: 741-749, 2003.
65. Dickson, D. W., Lee, S. C., Mattiace, L. A., Yen, S. H., and Brosnan, C. Microglia and cytokines in neurological disease, with special reference to AIDS and Alzheimer's disease. Glia, 7: 75-83, 1993.
66. Lahiri, D. K., Chen, D., Vivien, D., Ge, Y. W., Greig, N. H., and Rogers, J. T. Role of cytokines in the gene expression of amyloid beta-protein precursor: identification of a 5'-UTR-binding nuclear factor and its implications in Alzheimer's disease. J Alzheimers Dis, 5: 81-90, 2003.
67. Laliberte, R. E., Perregaux, D. G., Hoth, L. R., Rosner, P. J., Jordan, C. K., Peese, K. M., Eggler, J. F., Dombroski, M. A., Geoghegan, K. F., and Gabel, C. A. Glutathione s-transferase omega 1-1 is a target of cytokine release inhibitory drugs and may be responsible for their effect on interleukin-1beta posttranslational processing. J Biol Chem, 278: 16567-16578, 2003.
68. Haboubi, N. Y., Kaftan, S. M., and Schofield, P. F. Radiation colitis is another mimic of chronic inflammatory bowel disease. J Clin Pathol, 45: 272, 1992.
69. Brynskov, J., Tvede, N., Andersen, C. B., and Vilien, M. Increased concentrations of interleukin 1 beta, interleukin-2, and soluble interleukin-2 receptors in endoscopical mucosal biopsy specimens with active inflammatory bowel disease. Gut, 33: 55-58, 1992.
70. Matsuura, T., West, G. A., Youngman, K. R., Klein, J. S., and Fiocchi, C. Immune activation genes in inflammatory bowel disease. Gastroenterology, 104: 448-458, 1993.
71. Beagley, K. W. and Elson, C. O. Cells and cytokines in mucosal immunity and inflammation. Gastroenterol Clin North Am, 21: 347-366, 1992.
72. MacDermott, R. P. Alterations in the mucosal immune system in ulcerative colitis and Crohn's disease. Med Clin North Am, 78: 1207-1231, 1994.
73. Isaacs, K. L., Sartor, R. B., and Haskill, S. Cytokine messenger RNA profiles in inflammatory bowel disease mucosa detected by polymerase chain reaction amplification. Gastroenterology, 103: 1587-1595, 1992.
74. Indaram, A. V., Nandi, S., Weissman, S., Lam, S., Bailey, B., Blumstein, M., Greenberg, R., and Bank, S. Elevated basal intestinal mucosal cytokine levels in asymptomatic first-degree relatives of patients with Crohn's disease. World J Gastroenterol, 6: 49-52, 2000.
75. Indaram, A. V., Visvalingam, V., Locke, M., and Bank, S. Mucosal cytokine production in radiation-induced proctosigmoiditis compared with inflammatory bowel disease. Am J Gastroenterol, 95: 1221-1225, 2000.
76. Ito, T. and Ikeda, U. Inflammatory cytokines and cardiovascular disease. Curr Drug Targets Inflamm Allergy, 2: 257-265, 2003.
77. Hotamisligil, G. S., Shargill, N. S., and Spiegelman, B. M. Adipose expression of tumor necrosis factor-alpha: direct role in obesity-linked insulin resistance. Science, 259: 87-91, 1993.
78. Hotamisligil, G. S., Arner, P., Caro, J. F., Atkinson, R. L., and Spiegelman, B. M. Increased adipose tissue expression of tumor necrosis factor-alpha in human obesity and insulin resistance. J Clin Invest, 95: 2409-2415, 1995.
79. Hotamisligil, G. S., Murray, D. L., Choy, L. N., and Spiegelman, B. M. Tumor necrosis factor alpha inhibits signaling from the insulin receptor. Proc Natl Acad Sci U S A, 91: 4854-4858, 1994.
80. Lang, C. H., Dobrescu, C., and Bagby, G. J. Tumor necrosis factor impairs insulin action on peripheral glucose disposal and hepatic glucose output. Endocrinology, 130: 43-52, 1992.
81. Hotamisligil, G. S. and Spiegelman, B. M. Tumor necrosis factor alpha: a key component of the obesity-diabetes link. Diabetes, 43: 1271-1278, 1994.
82. Uysal, K. T., Wiesbrock, S. M., Marino, M. W., and Hotamisligil, G. S. Protection from obesity-induced insulin resistance in mice lacking TNF-alpha function. Nature, 389: 610-614, 1997.
83. Ruan, H. and Lodish, H. F. Insulin resistance in adipose tissue: direct and indirect effects of tumor necrosis factor-alpha. Cytokine Growth Factor Rev, 14: 447-455, 2003.
84. Ruan, H., Pownall, H. J., and Lodish, H. F. Troglitazone antagonizes tumor necrosis factor-alpha-induced reprogramming of adipocyte gene expression by inhibiting the transcriptional regulatory functions of NF-kappaB. J Biol Chem, 278: 28181-28192, 2003.
85. Ofei, F., Hurel, S., Newkirk, J., Sopwith, M., and Taylor, R. Effects of an engineered human anti-TNF-alpha antibody (CDP57 1) on insulin sensitivity and glycemic control in patients with NIDDM. Diabetes, 45: 881-885, 1996.
86. Suri, A. and Katz, J. D. Dissecting the role of CD4+ T cells in autoimmune diabetes through the use of TCR transgenic mice. Immunol Rev, 169: 55-65, 1999.
87. Jun, H. S., Santamaria, P., Lim, H. W., Zhang, M. L., and Yoon, J. W. Absolute requirement of macrophages for the development and activation of beta-cell cytotoxic CD8+ T-cells in T-cell receptor transgenic NOD mice. Diabetes, 48: 34-42, 1999.
88. Yoon, J. W., Jun, H. S., and Santamaria, P. Cellular and molecular mechanisms for the initiation and progression of beta cell destruction resulting from the collaboration between macrophages and T cells. Autoimmunity, 27: 109-122, 1998.
89. Rabinovitch, A. and Suarez-Pinzon, W. L. Role of cytokines in the pathogenesis of autoimmune diabetes mellitus. Rev Endocr Metab Disord, 4: 291-299, 2003.
90. Tsuchiya, S., Yamabe, M., Yamaguchi, Y., Kobayashi, Y., Konno, T., and Tada, K. Establishment and characterization of a human acute monocytic leukemia cell line (THP-1). Int J Cancer, 26: 171-176, 1980.
91. Schumann, R. R., Belka, C., Reuter, D., Lamping, N., Kirschning, C. J., Weber, J. R., and Pfeil, D. Lipopolysaccharide activates caspase-1 (interleukin-1-converting enzyme) in cultured monocytic and endothelial cells. Blood, 91: 577-584, 1998.
92. Yoza, B. K., Hu, J. Y., and McCall, C. E. Protein-tyrosine kinase activation is required for lipopolysaccharide induction of interleukin 1beta and NFkappaB activation, but not NFkappaB nuclear translocation. J Biol Chem, 271: 18306-18309, 1996.
93. Haversen, L., Ohlsson, B. G., Hahn-Zoric, M., Hanson, L. A., and Mattsby-Baltzer, I. Lactoferrin down-regulates the LPS-induced cytokine production in monocytic cells via NF-kappa B. Cell Immunol, 220: 83-95, 2002.
94. Guha, M., O'Connell, M. A., Pawlinski, R., Hollis, A., McGovern, P., Yan, S. F., Stem, D., and Mackman, N. Lipopolysaccharide activation of the MEK-ERK1/2 pathway in human monocytic cells mediates tissue factor and tumor necrosis factor alpha expression by inducing Elk-1 phosphorylation and Egr-1 expression. Blood, 98: 1429-1439, 2001.
95. Guha, M. and Mackman, N. LPS induction of gene expression in human monocytes. Cell Signal, 13: 85-94, 2001.
96. Wang, E., Ma, W. J., Aghajanian, C., and Spriggs, D. R. Posttranscriptional regulation of protein expression in human epithelial carcinoma cells by adenine-uridine-rich elements in the 3'-untranslated region of tumor necrosis factor-alpha messenger RNA. Cancer Res, 57: 5426-5433, 1997.
97. Dean, J. L., Wait, R., Mahtani, K. R., Sully, G., Clark, A. R., and Saklatvala, J. The 3' untranslated region of tumor necrosis factor alpha mRNA is a target of the mRNA-stabilizing factor HuR. Mol Cell Biol, 21: 721-730, 2001.
98. Osman, F., Jarrous, N., Ben-Asouli, Y., and Kaempfer, R. A cis-acting element in the 3'-untranslated region of human TNF-alpha mRNA renders splicing dependent on the activation of protein kinase PKR. Genes Dev, 13: 3280-3293, 1999.
99. Liu, J. H., Wei, S., Burnette, P. K., Gamero, A. M., Hutton, M., and Djeu, J. Y. Functional association of TGF-beta receptor II with cyclin B. Oncogene, 18: 269-275, 1999.
100. Wang, L. G., Liu, X. M., Kreis, W., and Budman, D. R. Down-regulation of prostate-specific antigen expression by finasteride through inhibition of complex formation between androgen receptor and steroid receptor-binding consensus in the promoter of the PSA gene in LNCaP cells. Cancer Res, 57: 714-719, 1997.
101. Wang, L. G., Liu, X. M., Wikiel, H., and Bloch, A. Activation of casein kinase II in ML-1 human myeloblastic leukemia cells requires IGF-1 and transferrin. J Leukoc Biol, 57: 332-334, 1995.
102. Kong, M., Barnes, E. A., Ollendorff, V., and Donoghue, D. J. Cyclin F regulates the nuclear localization of cyclin BI through a cyclin-cyclin interaction. Embo J, 19: 1378-1388, 2000.
103. McGovern, S. L. and Shoichet, B. K. Kinase inhibitors: not just for kinases anymore. J Med Chem, 46: 1478-1483, 2003.
104. Group, C. Phase III clinical trials of Meisoindigo on the treatment of chronic myeloid leukemia. J. Chinese Hematology, 18: 69-72, 1997.
105. Tang, X., Fenton, M. J., and Amar, S. Identification and functional characterization of a novel binding site on TNF-alpha promoter. Proc Natl Acad Sci USA, 100: 4096-4101, 2003.
106. Okayasu, I., Hatakeyama, S., Yamada, M., Ohkusa, T., Inagaki, Y., and Nakaya, R. A novel method in the induction of reliable experimental acute and chronic ulcerative colitis in mice. Gastroenterology, 98: 694-702, 1990.
107. Lichtiger, S., Present, D. H., Kornbluth, A., Gelernt, I., Bauer, J., Galler, G., Michelassi, F., and Hanauer, S. Cyclosporine in severe ulcerative colitis refractory to steroid therapy. N Engl J Med, 330: 1841-1845, 1994.
108. Cooper, H.S., et al., "Clinicopathologic study of dextran sulfate sodium experimental murine colitis," *Lab Invest*, Vol. 69, pp. 238-249, 1993.
109. Murthy, S., et al., "The efficacy of BATy1015 in dextran sulfate model of mouse colitis," *Inflamm Res* Vol. 46, No. 6, pp. 224-233, 1997.
110. Murthy, S. N., et al., "Treatment Of Dextran Sulfate Sodium-Induced Murine Colitis By Intracolonic Cyclosporine," *Digestive Diseases and Sciences*, Vol. 38, No. 9, pp. 1722-1734, 1993.

What is claimed is:

1. A method of treating an inflammatory bowel disease, the method comprising administering meisoindigo to an animal in need of such treatment, wherein meisoindigo is administered in an amount sufficient to treat the inflammatory bowel disease.

2. The method according to claim 1, wherein the animal is a human being.

3. The method according to claim 1, wherein the inflammatory bowel disease is selected from the group consisting of: Crohn's disease and ulcerative colitis.

4. The method according to claim 1, wherein the compound is administered at a concentration sufficient to inhibit a cytokine selected from the group consisting of: IL-1α, β, IL-2, IL-3, IL-6, IL-7, IL-9, IL-12, IL-17, IL-18, TNF-α, LT, LIF, Oncostatin, and IFNc1α, β, γ; but the amount is less than sufficient to substantially inhibit cyclin dependent kinases.

5. The method according to claim 1, where the compound is administered at a concentration sufficient to stimulate expression of a cytokine selected from the group consisting of: IL-4, IL-10, IL-11, W-13 and TGFβ; but the amount is less than sufficient to substantially inhibit cyclin dependent kinases.

6. The method according to claim 3, wherein the inflammatory bowel disease is Crohn's disease.

7. The method according to claim 1, wherein the amount is less than sufficient to inhibit 50% of cyclin dependent kinases (CDKs) selected from the group consisting of: CDK2, CDK4, and CDK6.

8. The method according to claim 7, wherein the amount is less than sufficient to inhibit 40% of cyclin dependent kinases selected from the group consisting of: CDK2, CDK4, and CDK6.

9. The method according to claim 8, wherein the amount is less than sufficient to inhibit 30% of cyclin dependent kinases selected from the group consisting of: CDK2, CDK4, and CDK6.

10. The method according to claim 7, wherein the cyclin dependent kinase is CDK2.

11. The method according to claim 7, wherein the cyclin dependent kinase is CDK4.

12. The method according to claim 7, wherein the cyclin dependent kinase is CDK6.

13. The method according to claim 1, further comprising an anti-inflammatory agent.

14. The method according to claim 13, wherein the anti-inflammatory agent is selected from the group consisting of: an analgesic; an antirheumatic agent; an gastrointestinal agent; a gout preparation; glucocorticoids; opthalmic preparation; respiratory agent; a nasal preparation; and a mucous membrane agent, wherein the analgesic is selected, from the group consisting of: naproxen, indomethacin, ibuprofen, ketorolac tromethamine, choline magnesium trisalicylate and rofecoxib; the antirheumatic agent is selected from the group consisting of: cyclosporine, sulfasalazine, valdecoxib, penicillamine and dexamethasone; the gastrointestinal agent is selected from the group consisting of mesalamine, balsalazide disodium and olsalazine sodium; the gout preparation is sulindac; the glucocorticoid is selected from the group consisting of: dexamethasone, dexamethasone phosphate, methylprednisolone acetate, hydrocortisone and hydrocortisone sodium phosphate; the nasal preparation is selected from the group consisting of beclomethasone dipropionate monohydrate, fluticasone propionate, triamcinolone acetonide, flunisolide, mometasone furoate monohydrate and budesonide; the opthalmic preparation is ketorolac tromethamine; the respiratory agent is nedocromil sodium; and the mucous membrane agent is selected from the group consisting of: alclometasone dipropionate, hydrocortisone butyrate, flurandrenolide, betamethasone valerate and clobetasol propionate.

* * * * *

SEQUENCE LISTING

<160> NUMBER OF SEQ ID NOS: 4

<210> SEQ ID NO 1
<211> LENGTH: 19
<212> TYPE: DNA
<213> ORGANISM: Artificial sequence
<220> FEATURE:
<223> OTHER INFORMATION: IL-6 Gene specific primer

<400> SEQUENCE: 1
tcaattcgtt ctgaagagg

```
<210> SEQ ID NO 2
<211> LENGTH: 18
<212> TYPE: DNA
<213> ORGANISM: Artificial sequence
<220> FEATURE:
<223> OTHER INFORMATION: IL-6 Gene specific primer

<400> SEQUENCE: 2
cccccaggag aagattcc                                              18

<210> SEQ ID NO 3
<211> LENGTH: 18
<212> TYPE: DNA
<213> ORGANISM: Artificial sequence
<220> FEATURE:
<223> OTHER INFORMATION: TNF-alpha specific primer

<400> SEQUENCE: 3
tgcccagact cggcaaag                                              18

<210> SEQ ID NO 4
<211> LENGTH: 18
<212> TYPE: DNA
<213> ORGANISM: Artificial sequence
<220> FEATURE:
<223> OTHER INFORMATION: TNF-alpha specific primer

<400> SEQUENCE: 4
ggagaagggt gaccgact                                              18
```